US008007509B2

(12) United States Patent
Buiser et al.

(10) Patent No.: US 8,007,509 B2
(45) Date of Patent: Aug. 30, 2011

(54) COIL ASSEMBLIES, COMPONENTS AND METHODS

(75) Inventors: Marcia S. Buiser, Watertown, MA (US); Steve Keenan, Framingham, MA (US); Ashley Seehusen, Newton, MA (US); Christopher Nardone, N. Chelmsford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 548 days.

(21) Appl. No.: 11/248,033

(22) Filed: Oct. 12, 2005

(65) Prior Publication Data
US 2007/0083226 A1     Apr. 12, 2007

(51) Int. Cl.
*A61M 29/00* (2006.01)
(52) U.S. Cl. ......... 606/200; 606/108; 606/191; 606/198
(58) Field of Classification Search .................. 606/191, 606/200, 32, 29; 604/104, 907
See application file for complete search history.

(56) References Cited

U.S. PATENT DOCUMENTS

| | | | |
|---|---|---|---|
| 2,609,347 A | 9/1952 | Wilson | |
| 3,663,470 A | 5/1972 | Nishimura et al. | |
| 3,737,398 A | 6/1973 | Yamaguchi | |
| 3,921,632 A | 11/1975 | Bardani | |
| 3,957,933 A | 5/1976 | Egli et al. | |
| 4,025,686 A | 5/1977 | Zion | |
| 4,034,759 A | 7/1977 | Haerr | |
| 4,055,377 A | 10/1977 | Erickson et al. | |
| 4,076,640 A | 2/1978 | Forgensi et al. | |
| 4,094,848 A | 6/1978 | Naito | |
| 4,096,230 A | 6/1978 | Haerr | |
| 4,098,728 A | 7/1978 | Rosenblatt | |
| 4,110,529 A | 8/1978 | Stoy | |
| 4,159,719 A | 7/1979 | Haerr | |
| 4,191,672 A | 3/1980 | Salome et al. | |
| 4,198,318 A | 4/1980 | Stowell et al. | |
| 4,243,794 A | 1/1981 | White et al. | |
| 4,246,208 A | 1/1981 | Dundas | |
| 4,266,030 A | 5/1981 | Tschang et al. | |
| 4,268,495 A | 5/1981 | Muxfeldt et al. | |
| 4,271,281 A | 6/1981 | Kelley et al. | |
| 4,402,319 A | 9/1983 | Handa et al. | |
| 4,413,070 A | 11/1983 | Rembaum | |
| 4,427,794 A | 1/1984 | Lange et al. | |
| 4,428,869 A | 1/1984 | Munteanu et al. | |
| 4,429,062 A | 1/1984 | Pasztor et al. | |
| 4,442,843 A | 4/1984 | Rasor et al. | |
| 4,444,961 A * | 4/1984 | Timm | |

(Continued)

FOREIGN PATENT DOCUMENTS

AU        A-76186/98        10/1998

(Continued)

OTHER PUBLICATIONS

U.S. Appl. No. 11/000,741 ("Embolic Coils", Elliott et al.), filed Dec. 1, 2004.

(Continued)

*Primary Examiner* — Darwin P Erezo
*Assistant Examiner* — Mark Mashack
(74) *Attorney, Agent, or Firm* — Vista IP Law Group LLP

(57) ABSTRACT

Coil assemblies and related components and methods are disclosed. The coil assemblies can include two or more embolic coils having one or more different coil parameters.

13 Claims, 12 Drawing Sheets

U.S. PATENT DOCUMENTS

| | | | |
|---|---|---|---|
| 4,452,773 A * | 6/1984 | Molday | |
| 4,456,693 A * | 6/1984 | Welsh | |
| 4,459,145 A * | 7/1984 | Elsholz | |
| 4,472,552 A * | 9/1984 | Blouin | |
| 4,477,255 A * | 10/1984 | Pasztor et al. | |
| 4,492,720 A * | 1/1985 | Mosier | |
| 4,522,953 A * | 6/1985 | Barby et al. | |
| 4,542,178 A * | 9/1985 | Zimmermann et al. | |
| 4,551,132 A * | 11/1985 | Pasztor et al. | |
| 4,551,436 A * | 11/1985 | Johnson et al. | |
| 4,573,967 A * | 3/1986 | Hargrove et al. | |
| 4,622,362 A * | 11/1986 | Rembaum | |
| 4,623,706 A * | 11/1986 | Timm et al. | |
| 4,640,807 A * | 2/1987 | Afghan et al. | |
| 4,657,756 A * | 4/1987 | Rasor et al. | |
| 4,661,137 A * | 4/1987 | Garnier et al. | |
| 4,663,358 A * | 5/1987 | Hyon et al. | |
| 4,671,954 A * | 6/1987 | Goldberg et al. | |
| 4,674,480 A * | 6/1987 | Lemelson | |
| 4,675,113 A * | 6/1987 | Graves et al. | |
| 4,678,710 A * | 7/1987 | Sakimoto et al. | |
| 4,678,814 A * | 7/1987 | Rembaum | |
| 4,680,320 A * | 7/1987 | Uku et al. | |
| 4,681,119 A * | 7/1987 | Rasor et al. | |
| 4,708,718 A * | 11/1987 | Daniels | |
| 4,742,086 A * | 5/1988 | Masamizu et al. | |
| 4,743,507 A | 5/1988 | Franses et al. | |
| 4,772,635 A | 9/1988 | Mitschker et al. | |
| 4,782,097 A | 11/1988 | Jain et al. | |
| 4,789,501 A | 12/1988 | Day et al. | |
| 4,793,980 A | 12/1988 | Torobin | |
| 4,795,741 A | 1/1989 | Leshchiner et al. | |
| 4,801,458 A | 1/1989 | Hidaka et al. | |
| 4,804,366 A | 2/1989 | Zdeb et al. | |
| 4,819,637 A | 4/1989 | Dormandy, Jr. et al. | |
| 4,822,535 A | 4/1989 | Ekman et al. | |
| 4,833,237 A | 5/1989 | Kawamura et al. | |
| 4,850,978 A | 7/1989 | Dudar et al. | |
| 4,859,711 A | 8/1989 | Jain et al. | |
| 4,863,972 A | 9/1989 | Itagaki et al. | |
| 4,897,255 A | 1/1990 | Fritzberg et al. | |
| 4,900,303 A | 2/1990 | Lemelson | |
| 4,929,400 A | 5/1990 | Rembaum et al. | |
| 4,933,372 A | 6/1990 | Feibush et al. | |
| 4,946,899 A | 8/1990 | Kennedy et al. | |
| 4,954,399 A | 9/1990 | Tani et al. | |
| 4,981,625 A | 1/1991 | Rhim et al. | |
| 4,990,340 A | 2/1991 | Hidaka et al. | |
| 4,994,069 A * | 2/1991 | Ritchart et al. | 606/191 |
| 4,999,188 A | 3/1991 | Sloldovnik et al. | |
| 5,007,940 A | 4/1991 | Berg | |
| 5,011,677 A | 4/1991 | Day et al. | |
| H915 H | 5/1991 | Gibbs | |
| 5,015,423 A | 5/1991 | Eguchi et al. | |
| 5,021,059 A | 6/1991 | Kensey et al. | |
| 5,032,117 A | 7/1991 | Motta | |
| 5,034,324 A | 7/1991 | Shinozaki et al. | |
| 5,047,438 A | 9/1991 | Feibush et al. | |
| 5,079,274 A | 1/1992 | Schneider et al. | |
| 5,091,205 A | 2/1992 | Fan | |
| 5,106,903 A | 4/1992 | Vanderhoff et al. | |
| 5,108,407 A | 4/1992 | Geremia et al. | |
| 5,114,421 A | 5/1992 | Polak | |
| 5,116,387 A | 5/1992 | Berg | |
| 5,120,349 A | 6/1992 | Stewart et al. | |
| 5,125,892 A | 6/1992 | Drudik | |
| 5,147,631 A | 9/1992 | Glajch et al. | |
| 5,147,937 A | 9/1992 | Frazza et al. | |
| 5,149,543 A | 9/1992 | Cohen et al. | |
| 5,158,573 A | 10/1992 | Berg | |
| 5,167,624 A | 12/1992 | Butler et al. | |
| 5,171,214 A | 12/1992 | Kolber et al. | |
| 5,171,217 A | 12/1992 | March et al. | |
| 5,181,921 A | 1/1993 | Makita et al. | |
| 5,190,760 A | 3/1993 | Baker | |
| 5,190,766 A | 3/1993 | Ishihara | |
| 5,192,301 A | 3/1993 | Kamiya et al. | |
| 5,202,352 A | 4/1993 | Okada et al. | |
| 5,216,096 A | 6/1993 | Hattori et al. | |
| 5,226,911 A | 7/1993 | Chee et al. | |
| 5,234,437 A | 8/1993 | Sepetka | |
| 5,250,071 A | 10/1993 | Palermo | |
| 5,253,991 A | 10/1993 | Yokota et al. | |
| 5,256,146 A | 10/1993 | Ensminger et al. | |
| 5,260,002 A | 11/1993 | Wang | |
| 5,261,916 A * | 11/1993 | Engelson | 606/108 |
| 5,262,176 A | 11/1993 | Palmacci et al. | |
| 5,263,964 A | 11/1993 | Purdy | |
| 5,263,992 A | 11/1993 | Guire | |
| 5,288,763 A | 2/1994 | Li et al. | |
| 5,290,310 A | 3/1994 | Makower et al. | |
| 5,292,332 A | 3/1994 | Lee | |
| 5,292,814 A | 3/1994 | Bayer et al. | |
| 5,302,369 A | 4/1994 | Day et al. | |
| 5,304,194 A * | 4/1994 | Chee et al. | 606/191 |
| 5,304,195 A | 4/1994 | Twyford, Jr. et al. | |
| 5,312,415 A * | 5/1994 | Palermo | 606/108 |
| 5,314,974 A | 5/1994 | Ito et al. | |
| 5,316,774 A | 5/1994 | Eury et al. | |
| RE34,640 E | 6/1994 | Kennedy et al. | |
| 5,320,639 A | 6/1994 | Rudnick | |
| 5,324,306 A | 6/1994 | Makower et al. | |
| 5,328,936 A | 7/1994 | Leifholtz et al. | |
| 5,334,216 A | 8/1994 | Vidal et al. | |
| 5,336,263 A | 8/1994 | Ersek et al. | |
| 5,342,394 A | 8/1994 | Matsuno et al. | |
| 5,344,452 A | 9/1994 | Lemperle | |
| 5,344,867 A | 9/1994 | Morgan et al. | |
| 5,350,397 A | 9/1994 | Palermo et al. | |
| 5,354,290 A | 10/1994 | Gross | |
| 5,354,295 A | 10/1994 | Guglielmi et al. | |
| 5,369,133 A | 11/1994 | Ihm et al. | |
| 5,369,163 A | 11/1994 | Chiou et al. | |
| 5,382,260 A | 1/1995 | Dormandy, Jr. et al. | |
| 5,384,124 A | 1/1995 | Courteille et al. | |
| 5,397,303 A | 3/1995 | Sancoff et al. | |
| 5,398,851 A | 3/1995 | Sancoff et al. | |
| 5,403,870 A | 4/1995 | Gross | |
| 5,411,520 A | 5/1995 | Nash et al. | |
| 5,417,982 A | 5/1995 | Modi | |
| 5,431,174 A | 7/1995 | Knute | |
| 5,435,645 A | 7/1995 | Faccioli et al. | |
| 5,443,495 A | 8/1995 | Buscemi et al. | |
| 5,456,693 A | 10/1995 | Conston et al. | |
| 5,468,801 A | 11/1995 | Antonelli et al. | |
| 5,469,854 A | 11/1995 | Unger et al. | |
| 5,476,472 A | 12/1995 | Dormandy, Jr. et al. | |
| 5,484,584 A | 1/1996 | Wallace et al. | |
| 5,490,984 A | 2/1996 | Freed | |
| 5,494,682 A | 2/1996 | Cohen et al. | |
| 5,494,940 A | 2/1996 | Unger et al. | |
| 5,512,604 A | 4/1996 | Demopolis | |
| 5,514,090 A | 5/1996 | Kriesel et al. | |
| 5,525,334 A | 6/1996 | Ito et al. | |
| 5,534,589 A | 7/1996 | Hager et al. | |
| 5,540,680 A | 7/1996 | Guglielmi et al. | |
| 5,541,031 A | 7/1996 | Yamashita et al. | |
| 5,542,935 A | 8/1996 | Unger et al. | |
| 5,553,741 A | 9/1996 | Sancoff et al. | |
| 5,556,391 A | 9/1996 | Cercone et al. | |
| 5,556,610 A | 9/1996 | Yan et al. | |
| 5,558,255 A | 9/1996 | Sancoff et al. | |
| 5,558,822 A | 9/1996 | Gitman et al. | |
| 5,558,856 A | 9/1996 | Klaveness et al. | |
| 5,559,266 A | 9/1996 | Klaveness et al. | |
| 5,567,415 A | 10/1996 | Porter | |
| 5,569,193 A | 10/1996 | Hofstetter et al. | |
| 5,569,449 A | 10/1996 | Klaveness et al. | |
| 5,569,468 A | 10/1996 | Modi | |
| 5,571,182 A | 11/1996 | Ersek et al. | |
| 5,580,575 A | 12/1996 | Unger et al. | |
| 5,583,162 A | 12/1996 | Li et al. | |
| 5,585,112 A | 12/1996 | Unger et al. | |
| 5,595,821 A | 1/1997 | Hager et al. | |
| 5,622,657 A | 4/1997 | Takada et al. | |
| 5,624,685 A | 4/1997 | Takahashi et al. | |
| 5,635,215 A | 6/1997 | Boschetti et al. | |

| | | | |
|---|---|---|---|
| 5,637,087 A | 6/1997 | O'Neil et al. | |
| 5,639,277 A * | 6/1997 | Mariant et al. ............... 606/191 | |
| 5,639,710 A | 6/1997 | Lo et al. | |
| 5,648,095 A | 7/1997 | Illum et al. | |
| 5,648,100 A | 7/1997 | Boschetti et al. | |
| 5,649,949 A * | 7/1997 | Wallace et al. ............... 606/191 | |
| 5,650,116 A | 7/1997 | Thompson | |
| 5,651,990 A | 7/1997 | Takada et al. | |
| 5,653,922 A | 8/1997 | Li et al. | |
| 5,657,756 A | 8/1997 | Vrba | |
| 5,681,576 A | 10/1997 | Henry | |
| 5,695,480 A | 12/1997 | Evans et al. | |
| 5,695,740 A | 12/1997 | Porter | |
| 5,698,271 A | 12/1997 | Liberti et al. | |
| 5,701,899 A | 12/1997 | Porter | |
| 5,715,824 A | 2/1998 | Unger et al. | |
| 5,716,981 A | 2/1998 | Hunter et al. | |
| 5,718,884 A | 2/1998 | Klaveness et al. | |
| 5,723,269 A | 3/1998 | Akagi et al. | |
| 5,725,534 A | 3/1998 | Rasmussen | |
| 5,733,925 A | 3/1998 | Kunz et al. | |
| 5,741,331 A | 4/1998 | Pinchuk | |
| 5,746,734 A | 5/1998 | Dormandy, Jr. et al. | |
| 5,749,891 A * | 5/1998 | Ken et al. ............... 606/200 | |
| 5,752,974 A | 5/1998 | Rhee et al. | |
| 5,760,097 A | 6/1998 | Li et al. | |
| 5,766,147 A | 6/1998 | Sancoff et al. | |
| 5,770,222 A | 6/1998 | Unger et al. | |
| 5,779,668 A | 7/1998 | Grabenkort | |
| 5,785,642 A | 7/1998 | Wallace et al. | |
| 5,785,682 A | 7/1998 | Grabenkort | |
| 5,792,478 A | 8/1998 | Lawin et al. | |
| 5,795,562 A | 8/1998 | Klaveness et al. | |
| 5,797,953 A | 8/1998 | Tekulve | |
| 5,800,453 A | 9/1998 | Gia | |
| 5,800,454 A | 9/1998 | Jacobsen et al. | |
| 5,800,455 A * | 9/1998 | Palermo et al. ............... 606/191 | |
| 5,807,323 A | 9/1998 | Kriesel et al. | |
| 5,813,411 A | 9/1998 | Van Bladel et al. | |
| 5,823,198 A | 10/1998 | Jones et al. | |
| 5,827,502 A | 10/1998 | Klaveness et al. | |
| 5,827,531 A | 10/1998 | Morrison et al. | |
| 5,830,178 A | 11/1998 | Jones et al. | |
| 5,833,361 A | 11/1998 | Funk | |
| 5,840,387 A | 11/1998 | Berlowitz-Tarrant et al. | |
| 5,846,518 A | 12/1998 | Yan et al. | |
| 5,853,752 A | 12/1998 | Unger et al. | |
| 5,855,615 A | 1/1999 | Bley et al. | |
| 5,863,957 A | 1/1999 | Li et al. | |
| 5,876,372 A | 3/1999 | Grabenkort et al. | |
| 5,877,224 A | 3/1999 | Brocchini et al. | |
| 5,885,216 A | 3/1999 | Evans, III et al. | |
| 5,885,547 A | 3/1999 | Gray | |
| 5,888,546 A | 3/1999 | Ji et al. | |
| 5,891,128 A * | 4/1999 | Gia et al. ............... 606/1 | |
| 5,891,130 A | 4/1999 | Palermo et al. | |
| 5,891,155 A | 4/1999 | Irie | |
| 5,894,022 A | 4/1999 | Ji et al. | |
| 5,895,385 A | 4/1999 | Guglielmi et al. | |
| 5,895,398 A | 4/1999 | Wensel et al. | |
| 5,895,411 A | 4/1999 | Irie | |
| 5,899,877 A | 5/1999 | Leibitzki et al. | |
| 5,902,832 A | 5/1999 | Van Bladel et al. | |
| 5,902,834 A | 5/1999 | Porrvik | |
| 5,922,025 A | 7/1999 | Hubbard | |
| 5,922,304 A | 7/1999 | Unger | |
| 5,925,059 A | 7/1999 | Palermo et al. | |
| 5,928,626 A | 7/1999 | Klaveness et al. | |
| 5,935,553 A | 8/1999 | Unger et al. | |
| 5,941,888 A * | 8/1999 | Wallace et al. ............... 606/108 | |
| 5,951,160 A | 9/1999 | Ronk | |
| 5,957,848 A | 9/1999 | Sutton et al. | |
| 5,959,073 A | 9/1999 | Schlameus et al. | |
| 6,003,566 A | 12/1999 | Thibault et al. | |
| 6,013,084 A * | 1/2000 | Ken et al. ............... 606/108 | |
| 6,015,546 A | 1/2000 | Sutton et al. | |
| 6,024,754 A * | 2/2000 | Engelson ............... 606/213 | |
| 6,027,472 A | 2/2000 | Kriesel et al. | |
| 6,028,066 A | 2/2000 | Unger | |
| 6,033,423 A * | 3/2000 | Ken et al. ............... 606/200 | |
| 6,047,861 A | 4/2000 | Vidal et al. | |
| 6,048,908 A | 4/2000 | Kitagawa | |
| 6,051,247 A | 4/2000 | Hench et al. | |
| 6,056,721 A | 5/2000 | Shulze | |
| 6,056,844 A | 5/2000 | Guiles et al. | |
| 6,059,766 A | 5/2000 | Greff | |
| 6,063,068 A | 5/2000 | Fowles et al. | |
| 6,071,495 A | 6/2000 | Unger et al. | |
| 6,071,497 A | 6/2000 | Steiner et al. | |
| 6,073,759 A | 6/2000 | Lamborne et al. | |
| 6,090,925 A | 7/2000 | Woiszwillo et al. | |
| 6,096,344 A | 8/2000 | Liu et al. | |
| 6,099,546 A | 8/2000 | Gia | |
| 6,099,864 A | 8/2000 | Morrison et al. | |
| 6,100,306 A | 8/2000 | Li et al. | |
| 6,139,963 A | 10/2000 | Fujii et al. | |
| 6,149,623 A | 11/2000 | Reynolds | |
| 6,159,206 A * | 12/2000 | Ogawa ............... 606/32 | |
| 6,160,084 A | 12/2000 | Langer et al. | |
| 6,162,377 A | 12/2000 | Ghosh et al. | |
| 6,165,193 A | 12/2000 | Greene, Jr. et al. | |
| 6,179,817 B1 | 1/2001 | Zhong | |
| 6,190,373 B1 | 2/2001 | Palermo et al. | |
| 6,191,193 B1 | 2/2001 | Lee et al. | |
| RE37,117 E | 3/2001 | Palermo | |
| 6,214,331 B1 | 4/2001 | Vanderhoff et al. | |
| 6,224,630 B1 | 5/2001 | Bao et al. | |
| 6,224,794 B1 | 5/2001 | Amsden et al. | |
| 6,231,586 B1 | 5/2001 | Mariant | |
| 6,235,224 B1 | 5/2001 | Mathiowitz et al. | |
| 6,238,403 B1 | 5/2001 | Greene, Jr. et al. | |
| 6,245,090 B1 | 6/2001 | Gilson et al. | |
| 6,254,592 B1 * | 7/2001 | Samson et al. ............... 606/1 | |
| 6,258,338 B1 | 7/2001 | Gray | |
| 6,261,585 B1 | 7/2001 | Sefton et al. | |
| 6,264,861 B1 | 7/2001 | Tavernier et al. | |
| 6,267,154 B1 | 7/2001 | Felicelli et al. | |
| 6,268,053 B1 | 7/2001 | Woiszwillo et al. | |
| 6,277,392 B1 | 8/2001 | Klein | |
| 6,280,457 B1 | 8/2001 | Wallace et al. | |
| 6,291,605 B1 | 9/2001 | Freeman et al. | |
| 6,296,604 B1 | 10/2001 | Garibaldi et al. | |
| 6,296,622 B1 | 10/2001 | Kurz et al. | |
| 6,296,632 B1 | 10/2001 | Luscher et al. | |
| 6,306,153 B1 * | 10/2001 | Kurz et al. ............... 606/191 | |
| 6,306,418 B1 | 10/2001 | Bley | |
| 6,306,419 B1 | 10/2001 | Vachon et al. | |
| 6,306,427 B1 | 10/2001 | Annonier et al. | |
| 6,312,407 B1 | 11/2001 | Zadno-Azizi et al. | |
| 6,315,709 B1 | 11/2001 | Garibaldi et al. | |
| 6,322,576 B1 * | 11/2001 | Wallace et al. ............... 606/191 | |
| 6,335,384 B1 | 1/2002 | Evans et al. | |
| 6,344,041 B1 * | 2/2002 | Kupiecki et al. ............... 606/32 | |
| 6,344,182 B1 | 2/2002 | Sutton et al. | |
| 6,355,275 B1 | 3/2002 | Klein | |
| 6,368,658 B1 | 4/2002 | Schwarz et al. | |
| 6,379,373 B1 | 4/2002 | Sawhney et al. | |
| 6,388,043 B1 | 5/2002 | Langer et al. | |
| 6,394,965 B1 | 5/2002 | Klein | |
| 6,423,332 B1 | 7/2002 | Huxel et al. | |
| 6,432,437 B1 | 8/2002 | Hubbard | |
| 6,436,112 B2 | 8/2002 | Wensel et al. | |
| 6,443,941 B1 | 9/2002 | Slepian et al. | |
| 6,476,069 B2 | 11/2002 | Krall et al. | |
| 6,544,503 B1 | 4/2003 | Vanderhoff et al. | |
| 6,544,544 B2 | 4/2003 | Hunter et al. | |
| 6,545,097 B2 | 4/2003 | Pinchuk et al. | |
| 6,551,305 B2 * | 4/2003 | Ferrera et al. ............... 606/1 | |
| 6,551,340 B1 * | 4/2003 | Konya et al. ............... 606/191 | |
| 6,575,896 B2 | 6/2003 | Silverman et al. | |
| 6,589,230 B2 | 7/2003 | Gia et al. | |
| 6,602,261 B2 | 8/2003 | Greene, Jr. et al. | |
| 6,602,524 B2 | 8/2003 | Batich et al. | |
| 6,605,111 B2 | 8/2003 | Bose et al. | |
| 6,629,947 B1 | 10/2003 | Sahatjian et al. | |
| 6,632,531 B2 | 10/2003 | Blankenship | |
| 6,635,069 B1 * | 10/2003 | Teoh et al. ............... 606/200 | |
| 6,638,291 B1 * | 10/2003 | Ferrera et al. ............... 606/191 | |

| | | | | | | | |
|---|---|---|---|---|---|---|---|
| 6,652,883 | B2 | 11/2003 | Goupil et al. | EP | 0 730 847 | | 9/1996 |
| 6,669,652 | B2 | 12/2003 | Anderson et al. | EP | 0 744 940 | | 12/1996 |
| 6,680,046 | B1 | 1/2004 | Boschetti | EP | 0 764 047 | | 3/1997 |
| 6,699,222 | B1 | 3/2004 | Jones et al. | EP | 0 797 988 | | 10/1997 |
| 7,029,486 | B2 * | 4/2006 | Schaefer et al. ............. 606/191 | EP | 0 820 726 | | 1/1998 |
| 7,053,134 | B2 | 5/2006 | Baldwin et al. | EP | 0 865 773 | | 9/1998 |
| 7,094,369 | B2 | 8/2006 | Buiser et al. | EP | 0 993 337 | | 4/2000 |
| 7,131,997 | B2 | 11/2006 | Bourne et al. | FR | 2 641 692 | | 7/1990 |
| 7,326,225 | B2 * | 2/2008 | Ferrera et al. ............... 606/200 | JP | 59-196738 | | 11/1984 |
| 2001/0001835 | A1 | 5/2001 | Greene, Jr. et al. | JP | 62-45637 | | 2/1987 |
| 2001/0016210 | A1 | 8/2001 | Mathiowitz et al. | JP | 4-74117 | | 3/1992 |
| 2001/0036451 | A1 | 11/2001 | Goupil et al. | JP | 6-57012 | | 3/1994 |
| 2001/0051670 | A1 | 12/2001 | Goupil et al. | JP | 9-110678 | | 4/1997 |
| 2002/0010481 | A1 | 1/2002 | Jayaraman | JP | 9-316271 | | 12/1997 |
| 2002/0082499 | A1 | 6/2002 | Jacobsen et al. | JP | 10-130329 | | 5/1998 |
| 2002/0197208 | A1 | 12/2002 | Ruys et al. | JP | 2000189511 | | 7/2000 |
| 2003/0007928 | A1 | 1/2003 | Gray | JP | 2001079011 | | 3/2001 |
| 2003/0018356 | A1 * | 1/2003 | Schaefer et al. ............. 606/200 | JP | 2002-017848 | | 1/2002 |
| 2003/0032935 | A1 | 2/2003 | Damiano et al. | TW | 421658 | | 2/2001 |
| 2003/0108614 | A1 | 6/2003 | Volkonsky et al. | WO | WO 91/12823 | | 5/1991 |
| 2003/0120302 | A1 * | 6/2003 | Minck et al. .................. 606/200 | WO | WO 92/21327 | | 12/1992 |
| 2003/0183962 | A1 | 10/2003 | Buiser et al. | WO | WO 93/19702 | | 10/1993 |
| 2003/0185895 | A1 | 10/2003 | Lanphere et al. | WO | WO 94/06503 | | 3/1994 |
| 2003/0185896 | A1 | 10/2003 | Buiser et al. | WO | WO 9406503 | A1 * | 3/1994 |
| 2003/0187320 | A1 | 10/2003 | Freyman | WO | WO 94/10936 | | 5/1994 |
| 2003/0194390 | A1 | 10/2003 | Krall et al. | WO | WO 95/03036 | | 2/1995 |
| 2003/0203985 | A1 | 10/2003 | Baldwin et al. | WO | WO 95/22318 | | 8/1995 |
| 2003/0206864 | A1 | 11/2003 | Mangin | WO | WO 95/33553 | | 12/1995 |
| 2003/0215519 | A1 | 11/2003 | Schwarz et al. | WO | WO 96/22736 | | 8/1996 |
| 2003/0233150 | A1 | 12/2003 | Bourne et al. | WO | WO 96/37165 | | 11/1996 |
| 2004/0076582 | A1 | 4/2004 | DiMatteo et al. | WO | WO 96/39464 | | 12/1996 |
| 2004/0091543 | A1 | 5/2004 | Bell et al. | WO | WO 98/04616 | | 2/1998 |
| 2004/0092883 | A1 | 5/2004 | Casey, III et al. | WO | WO 98/10798 | | 3/1998 |
| 2004/0096662 | A1 | 5/2004 | Lanphere et al. | WO | WO 98/26737 | | 6/1998 |
| 2004/0101564 | A1 | 5/2004 | Rioux et al. | WO | WO 98/47532 | | 10/1998 |
| 2004/0111044 | A1 | 6/2004 | Davis et al. | WO | WO 99/00187 | | 1/1999 |
| 2004/0153025 | A1 * | 8/2004 | Seifert et al. .................... 604/19 | WO | WO 99/12577 | | 3/1999 |
| 2004/0161451 | A1 | 8/2004 | Pierce et al. | WO | WO 99/42038 | | 8/1999 |
| 2004/0181174 | A2 | 9/2004 | Davis et al. | WO | WO 99/43380 | | 9/1999 |
| 2004/0186377 | A1 | 9/2004 | Zhong et al. | WO | WO 99/57176 | | 11/1999 |
| 2004/0243168 | A1 * | 12/2004 | Ferrera et al. ................. 606/191 | WO | WO 00/23054 | | 4/2000 |
| 2005/0025800 | A1 | 2/2005 | Tan | WO | WO 00/32112 | | 6/2000 |
| 2005/0033350 | A1 * | 2/2005 | Ken et al. ...................... 606/200 | WO | WO 00/40259 | | 7/2000 |
| 2005/0037047 | A1 | 2/2005 | Song | WO | WO 00/53105 | | 9/2000 |
| 2005/0095428 | A1 | 5/2005 | DiCarlo et al. | WO | WO 00/71196 | | 11/2000 |
| 2005/0129775 | A1 | 6/2005 | Lanphere et al. | WO | WO 00/74633 | | 12/2000 |
| 2005/0196449 | A1 | 9/2005 | DiCarlo et al. | WO | WO 01/12359 | | 2/2001 |
| 2005/0226935 | A1 | 10/2005 | Kamath et al. | WO | WO 01/66016 | | 9/2001 |
| 2005/0238870 | A1 | 10/2005 | Buiser et al. | WO | WO 01/70291 | | 9/2001 |
| 2005/0263916 | A1 | 12/2005 | Lanphere et al. | WO | WO 01/72281 | | 10/2001 |
| 2006/0045900 | A1 | 3/2006 | Richard et al. | WO | WO 01/76845 | | 10/2001 |
| 2006/0116711 | A1 | 6/2006 | Elliott et al. | WO | WO 01/93920 | | 12/2001 |
| 2006/0173090 | A1 | 8/2006 | Baldwin et al. | WO | WO 02/11696 | | 2/2002 |
| 2006/0199009 | A1 | 9/2006 | Anderson et al. | WO | WO 02/34298 | | 5/2002 |
| 2006/0199010 | A1 | 9/2006 | DiCarlo et al. | WO | WO 02/34299 | | 5/2002 |
| 2006/0210710 | A1 | 9/2006 | Buiser et al. | WO | WO 02/34300 | | 5/2002 |
| 2006/0247610 | A1 | 11/2006 | Lanphere et al. | WO | WO 02/43580 | | 6/2002 |
| 2006/0292300 | A1 | 12/2006 | Tan | WO | WO 02/096302 | | 12/2002 |
| 2007/0004973 | A1 | 1/2007 | Tan | WO | WO 03/013552 | | 2/2003 |
| 2007/0059375 | A1 | 3/2007 | Bourne et al. | WO | WO 03/051451 | | 6/2003 |
| 2007/0083219 | A1 | 4/2007 | Buiser et al. | WO | WO 03/082359 | | 10/2003 |
| | | | | WO | WO 2004/019999 | | 3/2004 |
| | | | | WO | WO 2004/040972 | | 5/2004 |
| | | | | WO | WO 2004/073688 | | 9/2004 |
| | | | | WO | WO 2005/009253 | | 2/2005 |

FOREIGN PATENT DOCUMENTS

| | | |
|---|---|---|
| DE | 233 303 | 2/1986 |
| DE | 3834705 | 4/1990 |
| DE | 94 14 868.6 | 12/1994 |
| DE | 100 26 620 | 3/2002 |
| EP | 0 067 459 | 12/1982 |
| EP | 0 122 624 | 10/1984 |
| EP | 0 123 235 | 10/1984 |
| EP | 0 402 031 | 12/1990 |
| EP | 0 422 258 | 4/1991 |
| EP | 0 458 079 | 11/1991 |
| EP | 0 458 745 | 11/1991 |
| EP | 0 470 569 | 2/1992 |
| EP | 0 547 530 | 6/1993 |
| EP | 0 600 529 | 6/1994 |
| EP | 0 623 012 | 11/1994 |
| EP | 0 706 376 | 4/1996 |

OTHER PUBLICATIONS

U.S. Appl. No. 11/070,967 ("Particles", Anderson et al.), filed Dec. 1, 2004.

U.S. Appl. No. 11/111,511 ("Particles", DiCarlo et al.), filed Apr. 21, 2005.

U.S. Appl. No. 11/117,156 ("Tissue-Treatment Methods", Lanphere et al.), filed Apr. 28, 2005.

U.S. Appl. No. 11/154,106 ("Tissue Treatment Methods", Tan), filed Jun. 15, 2005.

U.S. Appl. No. 11/165,949 ("Methods and Systems for Coating Particles", Tan), filed Jun. 24, 2005.

U.S. Appl. No. 11/274,538 ("Medical Articles Having Enhanced Therapeutic Agent Binding", Tenney et al.), filed Nov. 15, 2005.
Abbara et al., "Transcervical Expulsion of a Fibroid as a Result of Uterine Artery Embolization for Leiomyomata", *JVIR*, vol. 10, No. 4, pp. 409-411, 1999.
Abrahams, J.M. et al., "Topic Review: Surface Modifications Enhancing Biological Activity of Guglielmi Detachable Coils in Treating Intracranial Aneurysms", *Surg. Neurol.* 54:34-41, 2000.
Abrahams, J.M. et al., "Delivery of Human Vascular Endothelial Growth Factor with Platinum Coils Enhances Wall Thickening and Coil Impregnation in a Rat Aneurysm Model", *AJNR Am. J. Neuroradiol.* 22:1410-1417, Aug. 2001.
Ahuja, A.A., "Platinum Coil Coatings to Increase Thrombogenicity: A Preliminary Study in Rabbits", *AJNR Am. J. Neuroradiol.* 14:794-798; Jul./Aug. 1993.
Antibody Labeling, http://www.altcorp.com/AffinityLabeling/ablaeling.htm, pp. 1-6, May 20, 2003.
Bachtsi, A.R. et al., "An Experimental Investigation of Enzyme Release from Poly(vinyl alcohol) crosslinked Microspheres", *J. Microencapsulation*, vol. 12, No. 1, pp. 23-35; 1995.
Barr, J.D., et al., "Polyvinyl Alcohol Foam Particles Sizes and Concentrations Injectable through Microcatheters", *JVIR*, vol. 9, No. 1, pp. 113-118; 1998.
Barton, P. et al., "Embolization of Bone Metastases," *Journal of Vascular and Interventional Radiology*, 7(1):81-88 (Jan.-Feb. 1996).
Battinelli, L. et al., "New Class of Poly(vinyl alcohol) Polymrs as Column-Chromatography Stationary Phases for Candida Rugosa Lipase Isoforms Separation", *J. Chromatogr A*, vol. 753, No. 1, pp. 47-55; 1996.
Beaujeux, R. et al., "Trisacryl Gelatin Microspheres for Therapeutic Embolization, II: Preliminary Clinical Evaluation in Tumors and Arteriovenous Malformations," *AJNR Am. J. Neuroradiol.*, 17:541-548, Mar. 1996.
Berenstein, A. et al., "Catheter and Material Selection for Transarterial Embolization: Technical Considerations. II. Materials.", *Radiology*, vol. 132, No. 3, pp. 631-639; 1979.
Berenstein, A. et al., "Microembolization Techniques of Vascular Occlusion: Radiologic, Patohologic, and Clinical Correlation", *AJNR Am I Neuroradiol*, vol. 2, No. 3, pp. 261-267; 1981.
Berkowitz, R.P. et al., "Vaginal Expulsion of Submucosal Fibroids After Uterine Artery Embolization", *Journal of Reproductive Medicine*, vol. 44, No. 4, pp. 373-376; Apr. 1999 http://www.reproductivemedicine.com.
Bhattacharya et al., "Research & Aneurysms," *Interventional Neuroradiology*, 11(Suppl. 2):87-94 (Oct. 2005).
Boston Scientific Target, IDC™ Interlocking Coil, 1 page.
Bracard et al., "AVMs," *Interventional Neuroradiology*, 11(Suppl. 2):178-184 (Oct. 2005).
Bradley, E.A. et al., "Transcatheter Uterine Artery Embolisation to Treat Large Uterine Fibroids", *British Journal of Obstetrics and Gynaecology*, vol. 105, pp. 235-240; Feb. 1998.
Brockmann, J. et al., "Radiolabeling of p-Bz-DOTA-CD-11c antibody with $^{88}$Y: Conjugation, Labeling, Biodistribution studies", 2 pages, 2000 http://www.kernchemie.uni-mainz.de/downloads/jb2000/b14_brockmann.pdf.
Bruix, J. et al., "Transarterial Embolization Versus Symptomatic Treatment in Patients With Advanced Hepatocellular Carcinoma: Results of a Randomized, Controlled Trial in a Single Institution", *Hepatology*, Jun. 1998, vol. 27, No. 6, pp. 1578-1583, http://www.hepatitis-central.com/hcv/hcc/embolization/references.html.
Buhle, Jr. EL, "Re: Re: Hepatic Arterial Embolization", *UCLA Medicine Online*, Mar. 10, 1996, http://www.meds.com/archive/mol-cancer/1996/msg00128.html, 2 pages.
Burczak, et al., "Long-term in vivo performance and biocompatibility of poly (vinyl alcohol) hydrogel macrocapsules for hybrid-type artificial pancreas", *Biomaterials*; vol. 17, No. 24, pp. 2351-2356, 1996.
Burczak, et al., "Polymeric materials for biomedical purposes obtained by radiation methods. V. hybrid artificial pancreas", *Polim Med*, vol. 24, No. 1-2, pp. 45-55, 1994 (English Summary included).
Capozza et al., "Endoscopic treatment of vesico-ureteric reflux and urinary incontinence: technical problems in the paediatric patient," *British Journal of Urology*, 75(4):538-542 (Apr. 1995).

Carroll, B.A. et al., "Microbubbles as Ultrasonic Contrast Agents", *Investigative Radiology*, vol. 14, No. 3, p. 374, Supplement to May-Jun. 1979.
Carroll, B.A. et al., "Gelatin Encapsulated Nitrogen Microbubbles as Ultrasonic Contrast Agents", *Journal of Clinical and Laboratory Research*, vol. 15, No. 1, pp. 260-266, Feb. 1980.
Carstensen, E.L. et al., "Determination of the Acoustic Properties of Blood and its Components", *Journal of Acoustical Society of America*, vol. 25, No. 2, pp. 286-289, Mar. 1953.
Choe, et al., "An experimental study of embolic effect according to infusion rate and concentration of suspension in transarterial particulate embolization", *Invest Radiol*, vol. 32, No. 5, pp. 260-270, 1997.
Chuang et al., "Experimental Canine Hepatic Artery Embolization with Polyvinyl Alcohol Foam Particles", *Departments of Diagnostic Radiology and Veterinary Medicine*, The University of Texas, M.D. Anderson Hospital and Tumor Institute at Houston, Texas, pp. 21-25, Oct. 1982.
Cirkel, U. et al., "Experience with Leuprorelin Acetate Depot in the Treatment of Fibroids: A German Multicentre Study", *Clinical Therapeutics*, vol. 14, Suppl. A, 1992.
Clarian Health Methodist—Indiana Lions Gamma Knife Center, "Arteriovenous Malformation," http://www.clarian.com/tyhealth/gammaknife/cond_arter.asp, 4 pages, Last Updated on Mar. 20, 2000.
Collice et al., "Neurosurgery & Aneurysms," *Interventional Neuroradiology*, 11(Suppl. 2):226-231 (Oct. 2005).
Colombo M, "Treatment of Hepatocellular Carcinoma", *Journal of Viral Hepatitis*, 4(Suppl. 1):125-130 (1997), http://home.texoma.net/~moreland/stats/hcc-9.html.
Concentric Medical, Inc.—Product Information (3 pages), 2002.
Cotroneo et al., "Aneurysms," *Interventional Neuroradiology*, 11(Suppl. 2):212-216 (Oct. 2005).
Cruise et al., "In Vitro and In Vivo Characterization of a Hydrogel-Based Aneurysm Embolization System," *Society for Biomaterials 28$^{th}$ Annual Meeting Transactions*, p. 203 (2002).
Deasy, P. B., "*Microencapsulation and Related Drug Processes*", New York, NY, Marcel Dekker, Inc., 345 pages, 1984 (Table of Contents only).
de Gast, A.N. et al., "Transforming Growth Factor β-coated Platinum Coils for Endovascular Treatment of Aneurysms: An Animal Study", *Neurosurgery*, vol. 49, No. 3, pp. 690-696, Sep. 2001.
Derdeyn, et al., "Collagen-coated acrylic microspheres for embolotherapy: in vivo and in vitro characteristics", *American Journal of Neuroradiology*, vol. 18, No. 4, pp. 647-653, 1997.
Derdeyn, et al., "Polyvinyl alcohol particle size and suspension characteristics", *American Journal of Neuroradiology*, vol. 16, pp. 1335-1343, 1995.
DiLuccio et al., "Sustained-Release Oral Delivery of Theophylline by Use of Polyvinyl Alcohol and Polyvinyl Alcohol-Methyl Acrylate Polymers", *Journal of Pharmaceutical Sciences*, vol. 83, No. 1, pp. 104-106, Jan. 1994.
Ducati et al., "Aneurysms," *Interventional Neuroradiology*, 11(Suppl. 2):95-99 (Oct. 2005).
Duckwiler et al., "Catheters, embolic agents spark neurointervention," *Diagnostic Imaging*, 16(5):66-72 (May 1994).
Eskridge, "Interventional Neuroradiology," *Radiology*, 172:991-1006 (Nov. 1989).
Feldman, L. et al., "Transcatheter Vessel Occlusion: Angiographic Results Versus Clinical Success", *Radiology*, vol. 147, pp. 1-5, Apr. 1983.
Ferrofluids, Physical Properties and Applications Ferrofluidics Corp., Nashua, NH, 5 pages, 1986.
FeRx Incorporated, FERX Profile http://www.biotechshares.com/FERX.htm, 4 pages (Retrieved from the internet on Jun. 26, 2003).
"Fibroid Treatment Collective—Fibroid Embolization," 2 pages, http://www.fibroids.org.
Fritzsch, T. et al., "SH U 508, A Transpulmonary Echocontrast Agent", *Investigative Radiology*, vol. 25, Supplement 1, pp. S160-S161, Sep. 1990.
Fujimoto, S. et al., "Biodegradable Mitomycin C Microspheres Given Intra-Arterially for Inoperable Hepatic Cancer", *Cancer*, vol. 56, pp. 2404-2410, 1985.

Gander, et al., "Effect of polymeric network structure on drug release from cross-linked poly(vinyl alcohol) micromatrices", *Pharm Res*, vol. 6, No. 7, pp. 578-584, 1989.

Germano, et al., "Histopathological follow-up study of 66 cerebral arteriovenous malformations after therapeutic embolization with polyvinyl alcohol", *J Neurosurg*, vol. 76, No. 4, pp. 607-614, 1992.

Geschwind et al., "Chemoembolization of Liver Tumor in a Rabbit Model: Assessment of Tumor Cell Death with Diffusion-Weighted MR Imaging and Histologic Analysis", *Journal of Vascular and Interventional Radiology*, vol. 11, No. 10, pp. 1244-1255, Dec. 2000.

Gilbert, W.M. et al., "Angiographic Embolization in the Management of Hemorrhagic Complications of Pregnancy", *American Journal of Obstetrics and Gynecology*, vol. 166, No. 2, pp. 493-497, Feb. 1992.

Gohel, et al., "Formulation design and optimization of modified-release microspheres of diclofenac sodium", *Drug Dev Ind Pharm*, vol. 25, No. 2, pp. 247-251, 1999.

Goldberg, B.B., "Ultrasonic Cholangiography", *Radiology*, vol. 118, pp. 401-404, Feb. 1976.

Goodwin, et al., "Overview of embolic agents and their indications", *Eleventh Annual International Symposium on Endovascular Therapy*, pp. 303-306, 1999.

Goodwin, et al., "Preliminary experience with uterine artery embolization for uterine fibroids", *Journal of Vascular and Interventional Radiology*, vol. 8, No. 4, pp. 517-526, 1997.

Gramiak et al., "Echocardiography of the Aortic Root," *Investigative Radiology*, 3(5):356-366 (Sep.-Oct. 1968).

Gramiak, R. et al., "Ultrasound Cardiography: Contrast Studies in Anatomy and Function", *Radiology*, vol. 92, No. 5, pp. 939-948, Apr. 1969.

Grandfils, et al., "Preparation of poly (D,L) lactide microspheres by emulsion solvent evaporation, and their clinical implications as a convenient embolic material", *J Biomed Mater Res*, vol. 26, No. 4, pp. 467-479, 1992.

Greenwood, L.H. et al., "Obstetric and Nonmalignant Gynecologic Bleeding: Treatment with Angiographic Embolization", *Radiology*, vol. 164, No. 1, pp. 155-159, Jul. 1987.

Guglielmi Detachable Coils (GDC); http://www.neurosurgery.pitt.edu/endovascular/treatments/gdc.html, Jun. 2005, pp. 1-3.

Gupta et al., "Plasma-induced graft polymerization of acrylic acid onto poly(ethylene terephthalate) films: characterization and human smooth muscle cell growth on grafted films," *Biomaterials*, 23:863-871 (2002).

Halstenberg et al., "Biologically Engineered Protein-*graft*-Poly(ethylene glycol) Hydrogels: A Cell Adhesive and Plasmin-Degradable Biosynthetic Material for Tissue Repair," *Biomacromolecules*, 3(4):710-723 (2002).

Hamada et al., "Embolization with Cellulose Porous Beads, II: Clinical Trial," *AJNR Am. J. Neuroradiol.*, 17:1901-1906 (Nov. 1996).

Hirano et al., "Transcutaneous Intrafold Injection for Unilateral Vocal Fold Paralysis: Functional Results," *Ann. Otol. Rhinol Laryngol.*, 99(8):598-604 (Aug. 1990).

Hon-Man et al., "Miscellanea," *Interventional Neuroradiology*, 11(Suppl. 2):159-164 (Oct. 2005).

Horak et al., "Hydrogels in endovascular embolization. I. Spherical particles of poly (2-hydroxyethyl methacrylate) and their medico-biological properties", *Biomaterials*, 7(3):188-192 (May 1986).

Horak et al., "Hydrogels in endovascular embolization. II. Clinical use of spherical particles", *Biomaterials*, 7(6):467-470 (Nov. 1986).

"How Matrix™ Detachable Coils Work," 1 page.

Huang, et al., "Percutaneous endovascular embolization of intracerebral arteriovenous malformations. Experience in 72 cases", *Chin Med J*, vol. 108, No. 6, pp. 413-419, 1995.

"Injectable Tissue Implant Could Repair Ravages of Surgery", Clemson University, Biotech Week, Oct. 22, 2003, p. 117.

Jack, et al., "Radiolabeled polyvinyl alcohol particles: a potential agent to monitor embolization procedures", *Int J Rad Appl Instrum B*, vol. 13, No. 3, pp. 235-243, 1986.

Jiaqi, Y. et al., "A New Embolic Material: Super Absorbent Polymer (SAP) Microsphere and Its Embolic Effects," *Nippon Acta Radiologica*, 56:19-24 (1996) (English Abstract included).

Jones, S.K. et al., "Experimental Examination of a Targeted Hyperthermia System Using Inductively Heated Ferromagnetic Microspheres in Rabbit Kidney", *Phys. Med. Biol.*, vol. 46, No. 2, pp. 385-398, Feb. 2001, www.iop.org/Journals/pb.

Joy C, et al., "Use of Preoperative Embolization in the Treatment of Vascular Metastatic Lesions of the Spine," http://www.aaos.org/wordhtml/anmeet91/scipro/ppr472.htm, Mar. 12, 1991.

Kai, et al., "The utility of the microcrystalline cellulose sphere as a particulate embolic agent: an experimental study", *American Journal of Radiology*, vol. 21, No. 6, pp. 1160-1163, 2000.

Kallmes, D.F. et al., "In Vitro Proliferation and Adhesion of Basic Fibroblast Growth Factor-producing Fibroblasts on Platinum Coils", *Radiology*, vol. 206, No. 1, pp. 237-243, Jan. 1998.

Kallmes et al., "Platinum Coil-mediated Implantation of Growth Factor-secreting Endovascular Tissue Grafts: An in Vivo Study," *Radiology*, 207(2):519-523 (May 1998).

Kan, et al., "In vivo microscopy of the liver after injection of lipiodol into the hepatic artery and portal vein in the rat", *Acta Radiologica*, vol. 30, pp. 419-425, 1989.

Kerber, C., "Balloon Catheter with a Calibrated Leak", *Radiology*, vol. 120, pp. 547-550, Sep. 1976.

Kerber et al., "Polyvinyl Alcohol Foam: Prepackaged Emboli for Therapeutic Embolization", *American Journal Roentgenol*, vol. 130, pp. 1193-1194, Jun. 1978.

Kerber, "Flow-Controlled Therapeutic Embolization: A Physiologic and Safe Technique", *AJR*, vol. 134, pp. 557-561, Mar. 1980.

Kim, et al., "Composite poly(vinyl alcohol) beads for controlled drug delivery", *Pharm Res*, vol. 9. No. 1, pp. 10-16, 1992.

Kim et al., "Poly(vinyl alcohol) beads with core-shell structure for drug delivery," *Cosmetic and Pharmaceutical Applications of Polymers*, Plenum Press, New York, pp. 209-214 (1991).

Kochan, J.P. et al., "Interventional Neuroradiology: Current Practices and Techniques at Temple University Hospital," http://www.temple.edu/radiology/stroke.html, 5 pages.

Kominami et al., "Complications," *Interventional Neuroradiology*, 11(Suppl. 2):191-195 (Oct. 2005).

Krinick et al., "A polymeric drug delivery system for the simultaneous delivery of drugs activatable by enzymes and/or light," *J. Biomater. Sci. Polymer Edn*, 5(4):303-324 (1994).

Kuhn, R. et al., "Embolic Occlusion of the Blood Supply to Uterine Myomas: Report of 2 Cases", *Aust. NZ. J. Obstet. Gynaecol.*, vol. 39, No. 1, pp. 120-122, Feb. 1999.

Kurata, et al., "Preoperative embolization for meningiomas using PVA particles", *No Shinkei Geka*, vol. 20, No. 4, pp. 367-373, 1992 (English Abstract included).

Kurbatova, G.T. et al., "Magnetically-guided Anesthetics Based on Highly Dispersed Iron Powders Coated by Polyacrylamide", *Biofizika*, vol. 47, No. 2, pp. 331-337, Mar.-Apr. 2002 http://intapp.medscape.com/px/medlineapp (English Abstract included).

Kurosaki et al., "Evaluation of PVA-Gel Spheres as GI-Transit Time Controlling Oral Drug Delivery System", *Proceedings of the 19th International Symposium on Controlled Release of Bioactive Materials*, Orlando, Florida, pp. 273-274, Jul. 26-31, 1992.

Kusano, et al., "Low-dose particulate polyvinylalcohol embolization in massive small artery intenstinal hemorrahage. Experimental and clinical results", *Invest Radiol*, vol. 22, No. 5, pp. 388-392, 1987.

Labarre et al., "Complement activation by substituted polyacrylamide hydrogels for embolisation and implantation", *Biomaterials*, vol. 23, pp. 2319-2327, 2002.

Lammer, et al., "Transcatheteral embolization with polyvinyl alcohol—technic and experimental studies", *Rontgenblatter*, vol. 36, No. 1, pp. 10-14, 1983 (English Abstract included).

Latchaw et al., "Polyvinyl Foam Embolization of Vascular and Neoplastic Lesions of the Head, Neck, and Spine", *Radiology*, vol. 131, pp. 669-679, Jun. 1979.

Laurent, "Materials and biomaterials for interventional radiology," *Biomed. & Pharmacother.*, 52:76-88 (1998).

Lendlein, A. et al., "Biodegradable, Elastic Shape-Memory Polymers for Potential Biomedical Applications", *Science*, vol. 296, pp. 1673-1676, May 31, 2002.

Leung et al., "Determinants of Postembolization Syndrome after Hepatic Chemoembolization", *Journal of Vascular and Interventional Radiology*, vol. 12, No. 3, pp. 320-326, Mar. 2001.

Leventon, William, "Hemocompatible Coatings for Blood-Contacting Devices", *Medical Device & Diagnostic Industry: Coating Technologies—New Methods to Ensure Blood Compatibility*, vol. 25, No. 8, pp. 62-67, Aug. 2003.

Levy et al., "Transcatheter Uterine Artery Embolization for the Treatment of Symptomatic Uterine Fibroid Tumors," *Journal of Women's Imaging*, 2(4):168-175 (2000).

Lipman, "Uterine artery embolization for the treatment of symptomatic uterine fibroids: A review," *Applied Radiology*, 29(7):15-20 (Jul. 2000).

Lowery, C.L. et al., "Screening Tests for Intrauterine Growth Retardation: A Comparison of Umbilical Artery Doppler to Real-Time Ultrasound", *Echocardiography*, vol. 7, No. 2, pp. 159-164, Mar. 1990.

Marich, K.W. et al., "Real-Time Imaging with a New Ultrasonic Camera: Part I, In Vitro Experimental Studies on Transmission Imaging of Biological Structures", *Journal of Clinical Ultrasound*, vol. 3, No. 1, pp. 5-16, Mar. 1975.

Markoff, et al., "Uterine arteriovenous malformation successfully embolized with a liquid polymer, isobutyl 2-cyanoacrylate", *Am. J. Obstet. Gynecol.*, 155:659-660 (Sep. 1986).

Markus et al., "Experimental Aspects of High-Intensity Transient Signals in the Detection of Emboli," *J. Clin. Ultrasound.*, 23(2):81-87 (Feb. 1995).

Maruhashi, "Modified Polyvinyl Alcohols I and II," *Polyvinyl Alcohol—Developments*, John Wiley & Sons, Chichester, England, pp. 160-161 and pp. 186-191 (1992).

Marx, W. F. et al., "Endovascular Treatment of Experimental Aneurysms by Use of Biologically Modified Embolic Devices: Coil-mediated Intraaneurysmal Delivery of Fibroblast Tissue Allografts", *AJNR. Am. J. Neuroradiol.*, vol. 22, pp. 323-333, Feb. 2001.

Mather, P.T., Research Group Homepage, Basic Goals and Methods, http://www.ims.uconn.edu/~mather, 4 pages.

"Matrix® Detachable Coils," Boston Scientific, http://www.bostonscientific.com, 3 pages (Retrieved from the Internet on Jul. 13, 2005).

Matsumaru, et al., "Embolic materials for endovascular treatment of cerebral lesions", *J Biomater Sci Polym Ed*, vol. 8, No. 7, pp. 555-569, 1997.

Matsumoto, H. et al., "Basic Fibroblast Growth Factor Released from a Platinum Coil with a Polyvinyl Alcohol Core Enhances Cellular Proliferation and Vascular Wall Thickness: An In Vitro and In Vivo Study", *Neurosurgery*, vol. 53, No. 2, pp. 402-408, Aug. 2003.

Matsumoto, Y. et al., "Room-Temperature Ferromagnetism in Transparent Transition Metal-Doped Titanium Dioxide", *Science*, vol. 291, pp. 854-856, Feb. 2, 2001 www.sciencemag.org.

Mavligit, G. et al., "Gastrointestinal Leiomyosarcoma Metastatic to the Liver," *Cancer*, 75(8):2083-2088 (Apr. 15, 1995).

McIvor, J. et al., "Pregnancy After Uterine Artery Embolization to Control Haemorrhage from Gestational Trophoblastic Tumour", *British Journal of Radiology*, vol. 69, No. 823, pp. 624-629, Jul. 1996.

MerocelXL Sponge with Hytrol http://www.xomed.com/newproducts/merocelxl/merocelxl_earwick.asp, 3 pages, 2001.

"Micrus Corporation Announces Encouraging Results of a Modified Coil, Cerecyte, for the Treatment of Cerebral Aneurysms," Business Wire, 2 pages (Nov. 19, 2003).

Mid-America Interventional Radiological Society, "New Treatment for Uterine Fibroids Avoids Surgery," http://www.mirs.org/fibroids.htm, 6 pages, Submitted in Oct. 1999.

Moroz, P. et al., "Arterial Embolization Hyperthermia in Porcine Renal Tissue", *Journal of Surgical Research*, vol. 105, No. 2, pp. 209-214, Jun. 15, 2002.

Moroz, P. et al., "Hepatic Clearance of Arterially Infused Ferromagnetic Particles", *Int. J. Hyperthermia*, vol. 19, No. 1, pp. 23-24, Feb. 2003, http://www.tandf.co.uk/journals.

Nakabayashi, et al., "Evaluation of particulate embolic materials with MR imaging, scanning electron microscopy, and phase-contrast microscopy", *American Journal of Neuroradiology*, vol. 18, No. 3, pp. 485-491, 1997.

Nakstad, et al., "Embolization of intracranial arteriovenous malformations and fistulas with polyvinyl alcohol particles and platinum fibre coils", *Neuroradiology*, vol. 34, No. 4, pp. 348-351, 1992.

Namiki, "Application of Teflon Paste for Urinary Incontinence—Report of 2 Cases," *Uro. Int.*, 39:280-282 (1984).

Nash, et al., "Modifications of polystyrenic matrices for the purification of proteins. II. Effect of the degree of glutaraldehyde-poly(vinyl alcohol) crosslinking on various dye ligand chromatography systems", *J Chromatogr A*, vol. 776, No. 1, pp. 55-63, 1997.

Nikishin LF et al., "Interventional radiology in diffuse toxic goiter", *European Congress of Radiology*, Abstract 9041, 1999, http://www.ecr.org/conferences/ecr1999/sciprg/abs/p090041.htm, 7 pages.

Ophir, et al., "Ultrasonic backscatter from contrast producing collagen microspheres", *Ultrasonic Imaging*, vol. 2, pp. 67-77, 1980.

Oregon Health Sciences University, "Fibroid Embolization," http://www.uhmc.edu/dotter-fibroid, 34 pages.

Orsini, L. F. et al., "Pelvic Organs in Premenarcheal Girls: Real-Time Ultrasonography", *Radiology*, vol. 153, No. 1, pp. 113-116, Oct. 1984.

Parker, et al., "A particulate contrast agent with potential for ultrasound imaging of liver", *Ultrasound in Medicine and Biology*, vol. 13, No. 9, pp. 555-566, 1987.

Pasquini et al., "Aneurysms," *Interventional Neuroradiology*, 11(Suppl. 2):136-143 (Oct. 2005).

Pedley et al., "Hydrogels in Biomedical Applications," *British Polymer Journal*, 12:99-110 (Sep. 1980).

Pérez Higueras et al., "Fistulae," *Interventional Neuroradiology*, 11(Suppl. 2):123-129 (Oct. 2005).

Pesant A.C. et al., "Dural fistulas involving the cavernous sinus: Treatment by embolization—7 cases", *European Congress of Radiology*, Abstract 3-088, 1997, http://www.ecr.org/conferences/ecr1997/sciprg/abs/9703088p.htm, 1 page.

Phillips, D. R. et al., "Experience with Laparoscopic Leiomyoma Coagulation and Concomitant Operative Hysteroscopy", *J. Am. Assoc. Gynecol. Laparosc*, vol. 4, No. 4, pp. 425-533, Aug. 1997.

Physicians' Desk Reference Family Guide to Women's Health, "Chapter 7—Common Disorders of the Reproductive System," http://www.healthsquare.com/pdrfg/wh/chapters/wh1ch01.htm, 24 pages.

Piske et al., "CT & MRI," *Interventional Neuroradiology*, 11(Suppl. 2):100-106 (Oct. 2005).

Politano et al., "Periurethral Teflon Injection for Urinary Incontinence," *The Journal of Urology*, 111:180-183 (1974).

Poppe, W. et al., "Pregnancy after Transcatheter Embolization of a Uterine Arteriovenous Malformation", *Am. J. Obstet. Gynecol.*, vol. 156, No. 5, pp. 1179-1180, May 1987.

Pritchard, et al., "Poly(Vinyl Alcohol): Basic Properties and Uses", London, England: Gordon and Breach Science Publishers, pp. 95-97, 1970.

Progelhof et al., "Table 4.21. Properties of electrical insulating films (101)," *Polymer Engineering Principles: Properties, Processes, and Tests for Design*, Hanser Publishers, Munich, p. 383 (1993).

Pryor J. and Berenstein A., "Epistaxis (Nose-bleeds)," http://www.wehealny.org/inn/Radiology/nosebleeds.html, 1 page.

"Pulmonary artery pseudoaneurysm/aneurysm," http://www.mamc.amedd.army.mil/williams/chest/vascular/paaneurysm/paaneyrysm.htm, 2 pages.

Purdy, et al., "Arteriovenous malformations of the brain: choosing embolic materials to enhance safety and ease of excision", *J Neurosurg*, vol. 77, No. 2, pp. 217-222, 1992.

Quisling, et al., "Histopathology analysis of intraarterial polyvinyl alcohol microemboli in rat cerebral cortex", *American Journal of Neuroradiology*, vol. 5, pp. 101-104, 1984.

Rajan et al., "Sarcomas Metastatic to the Liver: Response and Survial after Cisplatin, Doxorubicin, Mitomycin-C, Ethiodol, and Polyvinyl Alcohol Chemoembolization", *Journal of Vascular and Interventional Radiology*, vol. 12, No. 2, pp. 187-193, Feb. 2001.

Ramos, et al., "Tumor vascular signals in renal masses: detection with Doppler US", *Radiology*, vol. 168, No. 3, pp. 633-637, 1988.

Ravina, J.H. et al., "Advantage of Pre-Operative Embolization of Fibroids: About a Multicentric Set of 31 Cases", *Contracept. Fertil. Sex.*, vol. 23, No. 1, pp. 45-49, Jan. 1995 (English Abstract included).

Ravina, J.H. et al., "Arterial Embolisation to Treat Uterine Myomata", *Lancet*, vol. 346, pp. 671-674, Sep. 9, 1995.

Ravina, J.H. et al., "Interest of Particulate Arterial Embolization in the Treatment of Some Uterine Myoma", *Bull. Acad. Natle. Med.*, vol. 181, No. 2, pp. 233-246, Feb. 4, 1997 (English Summary included).

Repa, I. et al., "Mortalities Associated with Use of a Commercial Suspension of Polyvinyl Alcohol," *Radiology*, 170(2):395-399 (Feb. 1989).

Rhine et al., "Polymers for Sustained Macromolecule Release: Procedures to Fabricate Reproducible Delivery Systems and Control Release Kinetics," *Journal of Pharmaceutical Sciences*, 69(3):265-270 (Mar. 1980).

Rump, A. et al., "Pharmacokinetics of Intraarterial Mitomycin C in the Chemoembolisation Treatment of Liver Metastases," *Gen. Pharmac.*, 27(4):669-671 (1996).

Schetky, "Shape-Memory Alloys," *Encyclopedia of Chemical Technology*, Third Edition, vol. 20, John Wiley & Sons, New York, pp. 726-736 (1982).

Schlief, R. et al., "Enhanced Color Doppler Echocardiography of the Left Heart After Intravenous Injection of a New Saccharide Based Agent in Humans", *Circulation*, vol. 82, No. 2, p. 28, Oct. 1990 (Abstract).

Schlief, R. et al., "Successful Opacification of the Left Heart Chamber on Echocardiographic Examination after Intravenous Injection of a New Saccharide Based Contrast Agent", *Echocardiography*, vol. 7, No. 1, pp. 61-64, Jan. 1990.

Schwarz et al., "The acoustic filter: An ultrasonic blood filter for the heart-lung machine," *J. Thorac. Cardiovasc. Surg.*, 104(6):1647-1653 (Dec. 1992).

Sellar et al., "Fistulae," *Interventional Neuroradiology*, 11 (Suppl. 2):130-135 (Oct. 2005).

Shafik, "Intraesophageal Polytef injection for the treatment of reflux esophagitis," *Surg. Endosc.*, 10:329-331 (1996).

Shape Shifters, http://www.sciam.com/tehbiz/0501scicit6.html, 3 pages, 2001.

Shung, K.K. et al., "Scattering of Ultrasound by Blood", *IEEE Transactions on Biomedical Engineering*, vol. BME-23, No. 6, pp. 460-467, Nov. 1976.

Sigelmann, R.A. et al., "Analysis and Measurement of Ultrasound Backscattering from an Ensemble of Scatters Excited by Sine-Wave Bursts", *Journal of Acoustical Society of America*, vol. 53, No. 4, pp. 1351-1355, Apr. 1973.

SIR-Spheres (Yttrium-90 Microspheres), pp. 1-12.

SIR-Spheres, Radioactive Implant (Yttrium-90 Microspheres), Sirex Medical, Inc., San Diego, CA, Nov. 6, 2000, pp. 1-15.

Sirtex Medical Limited—Product Description http://www.sirtex.com/?p=72, 3 pages (Retrieved from the internet on May 27, 2003).

Sirtex Medical Limited—Targeted Radiotherapy with SIR-Spheres http://www.sirtex.com/?p=57, 2 pages (Retrieved from the internet on May 27, 2003).

Skotland, T. et al., "In Vitro Stability Analyses as a Model for Metabolism of Ferromagnetic Particles (Clariscan™), a Contrast Agent for Magnetic Resonance Imaging", *J. Pharm. Biomed. Anal.*, vol. 28, No. 2, pp. 323-329, Apr. 15, 2002.

"Smart Sutures Tie Themselves", Apr. 26, 2002, http://www.sciam.com/article.cfm?articleID=00047706-121F-1CD0-B4A8809EC588, 2 pages.

Smith et al., "Evaluation of Polydimethylsiloxane as an alternative in the Endoscopic Treatment of Vesicoureteral Reflux," *The Journal of Urology*, 152:1221-1224 (Oct. 1994).

Smith et al., "Left Heart Opacification with Peripheral Venous Injection of a New Saccharide Echo Contrast Agent in Dogs", *JACC*, vol. 13, No. 7, pp. 1622-1628, Jun. 1989.

Spickler, et al., "The MR appearance of endovascular embolic agents in vitro with clinical correlation", *Comput Med Imaging Graph*, vol. 14, No. 6, pp. 415-423, 1990.

Spies JB, "Georgetown University Medical Center. Uterine Fibroid Embolization (UFE). An alternative to surgery for patients with uterine fibroids. Literature Review," http://www.fibroidoptions.com/pr-lit.htm, 6 pages, Sep. 1, 2001.

Stancato-Pasik, A. et al., "Obstetric Embolotherapy: Effect on Menses and Pregnancy", *Radiology*, vol. 204, No. 3, pp. 791-793, Sep. 1997.

Stein, R. et al., "Targeting Human Cancer Xenografts with Monoclonal Antibodies Labeled Using Radioiodinated, Diethylenetriaminepentaacetic Acid-appended Peptides", *Clinical Cancer Research*, vol. 5, No. 10, pp. 3079-3087, Oct. 1999 (Supplement).

Strasnick et al., "Transcutaneous Teflon® Injection for Unilateral Vocal Cord Paralysis: An Update," *The Laryngoscope*, 101:785-787 (Jul. 1991).

Stridbeck, H. et al, "Collateral Circulation Following Repeated Distal Embolization of the Hepatic Artery in Pigs," *Invest. Radiol.*, 19(3):179-183 (1984).

Strother et al., "Aneurysms," *Interventional Neuroradiology*, 11(Suppl. 2):200-205 (Oct. 2005).

Strunk, et al., "Treatment of congenital coronary arteriovenous malformations with microparticle embolization", *Cathet Cardiovasc Diagn*, vol. 22, No. 2, pp. 133-136, 1991.

Swanson DA et al., "The role of embolization and nephrectomy in the treatment of metastatic renal carcinoma", *Urologic Clinics of North America*, 7(3):719-730, 1980. University of Pennsylvania Cancer Center—Oncolink, http://www.oncolink.upenn.edu/pdg_html/cites/00/00585.html.

Tabata et al., "Tumor accumulation of poly(vinyl alcohol) of different sizes after intravenous injection", *Journal of Controlled Release*, vol. 50, pp. 123-133, Jan. 2, 1998.

Tadavarthy et al., "Polyvinyl Alcohol (Ivalon)—A New Embolic Material", *The American Journal of Roentgenology Radium Therapy and Nuclear Medicine*, vol. 125, No. 3, pp. 609-616, Nov. 1975.

Tadavarthy et al., "Polyvinyl Alcohol (Ivalon) as an Embolizing Agent", *Seminars in Interventional Radiology*, vol. 1, No. 2, pp. 101-109, Jun. 1984.

Tamatani, S. et al., "Histological Interaction of Cultured Endothelial Cells and Endovascular Embolic Materials Coated with Extracellular Matrix", *J. Neurosurg.*, vol. 86, No. 1, pp. 109-112, Jan. 1997.

Tamatani et al., "Radiologic and Histopathologic Evaluation of Canine Artery Occlusion after Collagen-Coated Platinum Microcoil Delivery," *American Journal of Neuroradiology*, 20:541-545 (1999).

Tanaka et al., "Radiologic Placement of Side-Hole Catheter With Tip Fixation for Hepatic Arterial Infusion Chemotherapy," *JVIR*, vol. 14, pp. 63-68, 2003.

Tao, et al., "Study of microspheres for embolization of hepatic artery", *Acta Pharmaceutica Sinica*, vol. 23, No. 1, pp. 55-60, 1988.

Tao, et al., "Study of microspheres for embolization of hepatic artery", (Translation) *Acta Pharmaceutica Sinica*, vol. 23, No. 1, pp. 55-60, 1988.

Terada, et al., "Preoperative embolization of meningiomas fed by ophthalmic branch arteries", *Surg Neurol*, vol. 45, No. 2, pp. 161-166, 1996.

Thanoo, et al., "Controlled release of oral drugs from cross-linked polyvinyl alcohol microspheres", *J Pharm Pharmacol*, vol. 45, No. 1, pp. 16-20, 1993.

Thanoo, B. C. et al., "Preparation and Properties of Barium Sulphate and Methyl Iothalamate Loaded Poly(vinyl Alcohol) Microspheres as Radiopaque Particulate Emboli," *Journal of Applied Biomaterials*, 2:67-72 (1991).

Thanoo, et al., "Tantalum loaded silicone micropsheres as particulate emboli", *J Microencapsul*, vol. 8, No. 1, pp. 95-101, 1991.

Thelen, V.M. et al., "Catheter Embolisation of Metastasising Renal Carcinomas Using Butyle-2-cyano-acrylate", *Fortschr. Rontgenstr.*, vol. 124, No. 3, pp. 232-235, Mar. 1976 (English Abstract included).

The Fibroid Embolization Center of the New York United Hospital Medical Center, "Fibroid Facts," http://www.uhmc.com/fibro2.htm, 9 pages.

The Vanderbilt-Ingram Cancer Center, "Kidney Cancer," http://www.mc.Vanderbilt.Edu/cancer/cancerinfo/kidney.html, 1 page, 2001.

Tikkakoski, et al., "Preoperative embolization in the management of neck paragangliomas", *Laryngoscope*, vol. 107, pp. 821-826, 1997.

Toon, "Improving a Key Weapon Against Cancer," Research Horizons, pp. 11-12, Spring/Summer 2001.

Touho, et al., "Intravascular treatment of spinal arteriovenous malformations using a microcatheter—with special reference to serial xylocaine tests and intravascular pressure monitoring", *Surgical Neurology*, vol. 42, No. 2, pp. 148-156, 1994.

Tournade et al., "Miscellanea," *Interventional Neuroradiology*, 11(Suppl. 2):107-111 (Oct. 2005).

UCLA Radiological Sciences, "A summary of terms appearing in this text," http://www.radsci.ucla.edu:8000/aneurysm/terms.html, 1 page.

University Medical Center SUNY Stony Brook, Department of Urology, "Variococele and its treatment," http://www.hsc.sunysb.edu/urology/male_inf. . . variocoele_and_its_treatment.html, 8 pages, Last Updated on Mar. 12, 2001.

Vivas S et al., "Arterioportal fistula and hemobilia in a patient with hepatic transplant", Gastroenterol Hepatol, 21(2):88-9, http://www.doyma.es/copiani/revistas/gastro/abstr/abs_p080.html, Feb. 1998 (English Abstract included).

Vogel F, "Nonsurgical Management of Uterine Fibroids," http://www.holyname.org/brochure/fibroids.html, 5 pages.

Wakhloo, et al., "Extended preoperative polyvinyl alcohol microembolization of intracranial meningiomas: Assessment of two embolization techniques", *American Journal of Neuroradiology*, vol. 14, pp. 571-582, 1993.

Walker WJ, "Non Surgical Treatment of Fibroids in the UK by Uterine Artery Embolisation—An Alternative to Hysterectomy, Myomectomy and Myolysis," http://www.fibroids.co.uk/thepaper.html, 2 pages, 2002.

Walsh RM et al., "Role of Angiography and Embolization for Acute Massive Upper Gastronintestinal Hemorrhage," *J. Gastrointest. Surg.*, 3:61-66 (1999).

Waltman, A.C. et al., "Technique for Left Gastric Artery Catheterization", *Radiology*, vol. 109, No. 3, pp. 732-734, Dec. 1973.

White, Jr., "Embolotherapy in Vascular Disease," *American Journal of Roentgenology*, 142:27-30 (Jan. 1984).

Widder, K.J. et al., "Selective Targeting of Magnetic Microspheres Containing Adriamycin: Total Remission in Yoshida Sarcoma-Bearing Rats", *Proceedings of the 16th Annual Meeting of American Society of Clinical Oncology*, May 26-27, 1980, San Diego, CA, p. 261.

Widder, K. et al., "Magnetic Microspheres: Synthesis of a Novel Parenteral Drug Carrier", *Journal of Pharmaceutical Sciences*, vol. 68, No. 1, pp. 79-82, Jan. 1979.

Wikholm G et al., "Embolization of Cerebral Arteriovenous Malformations: Part I—Technique, Morphology, and Complications", *Neurosurgery*, 39(3):448-459 (Sep. 1996).

Winters et al., "Periurethral injection of collagen in the treatment of intrinsic sphincteric deficiency in the female patient," *The Urologic Clinics of North America*, 22(3):673-678 (Aug. 1995).

Worthington-Kirsch RL, "Interventionalists offer management option for uterine fibroids," *Diagnostic Imaging*, 21(3):47-49, Mar. 1999, http://www.dimag.com/references/9903wortrefs.html.

Worthington-Kirsch, et al., "Uterine arterial embolization for the management of leiomyomas: Quality-of-life assessment and clinical response", *Radiology*, vol. 208, No. 3, 625-629, 1998.

Wright, K.C. et al., "Partial Splenic Embolization Using Polyvinyl Alcohol Foam, Dextran, Polystyrene, or Silicone," *Radiology*, 142:351-354, Feb. 1982.

Wu, A.M., "Engineered Antibodies for Breast Cancer Imaging and Therapy," http://www.cbcrp.org/research/PageGrant.asp?grant_id=111, 3 pages, 1996.

Yamada, T. et al., "Extended Intraarterial Cisplatin Infusion for Treatment of Gynecologic Cancer After Altercation of Intrapelvic Blood Flow and Implantation of a Vascular Access Device", *Cardiovasc. Intervent. Radiol.*, vol. 19, pp. 139-145, 1996.

Yamashita, Y. et al., "Transcatheter Arterial Embolization of Obstetric and Gynaecological Bleeding: Efficacy and Clinical Outcome", *British Journal of Radiology*, vol. 67, pp. 530-534, Jun. 1994.

Yoon et al., "Surface Immobilization of Galactose onto Aliphatic Biodegradable Polymers for Hepatocyte Culture," *Biotechnol. Bioeng.*, 78(1):1-10 (Apr. 5, 2002).

Yusi et al., "Submuscosal Injection of Polyvinyl Alcohol in Artificially Created Vesico-Ureteral Reflux: A Preliminary Report," *Asian J. Surg.*, 18(2):122-127 (Apr. 1995).

Zisch et al., "Covalently conjugated VEGF-fibrin matrices for endothelialization," *Journal of Controlled Release*, 72:101-113 (2001).

Ziskin, M.C. et al., "Contrast Agents for Diagnostic Ultrasound", *Investigative Radiology*, vol. 7, No. 6, pp. 500-505, Nov.-Dec. 1972.

Zou, Ying-hua, et al. "Experimental Canine Hapatic Artery Embolization with Polyvinyl Alcohol Microspheres," *Zhong Hua Fang-She Xue ZaZhi*, 23(6):330-332 (1989).

Zou, Ying-hua, et al. "Experimental Canine Hapatic Artery Embolization with Polyvinyl Alcohol Microspheres," Translation, *Zhong Hua Fang-She Xue ZaZhi*, 23(6):330-332 (1989).

Cekirge et al., "Interlocking Detachable Coil Occlusion in the Endovascular Treatment of Intracranial Aneurysms: Preliminary Results," *AJNR Am. J. Neuroradiol.*, 17:1651-1657 (Oct. 1996).

Marks et al., "A Mechanically Detachable Coil for the Treatment of Aneurysms and Occlusion of Blood Vessels," *AJNR Am. J. Neuroradiol.*, 15:821-827 (May 1994).

Murphy, "Endovascular procedures," Johns Hopkins Interventional Neuroradiology [online], http://www.brainaneurysms.net/procedures/neurovasc_aneurysm.htm, 2 pages (retrieved from the Internet on Feb. 17, 2005).

Murphy et al., "Mechanical Detachable Platinum Coil: Report of the European Phase II Clinical Trial in 60 Patients," *Radiology*, 219:541-544 (2001).

"Providing Superior Coils, Components, and Assemblies for Medical Devices," Heraeus Vadnais, Inc. [online], http://www.vadtec.com, 6 pages (retrieved from the Internet on Feb. 22, 2005).

* cited by examiner

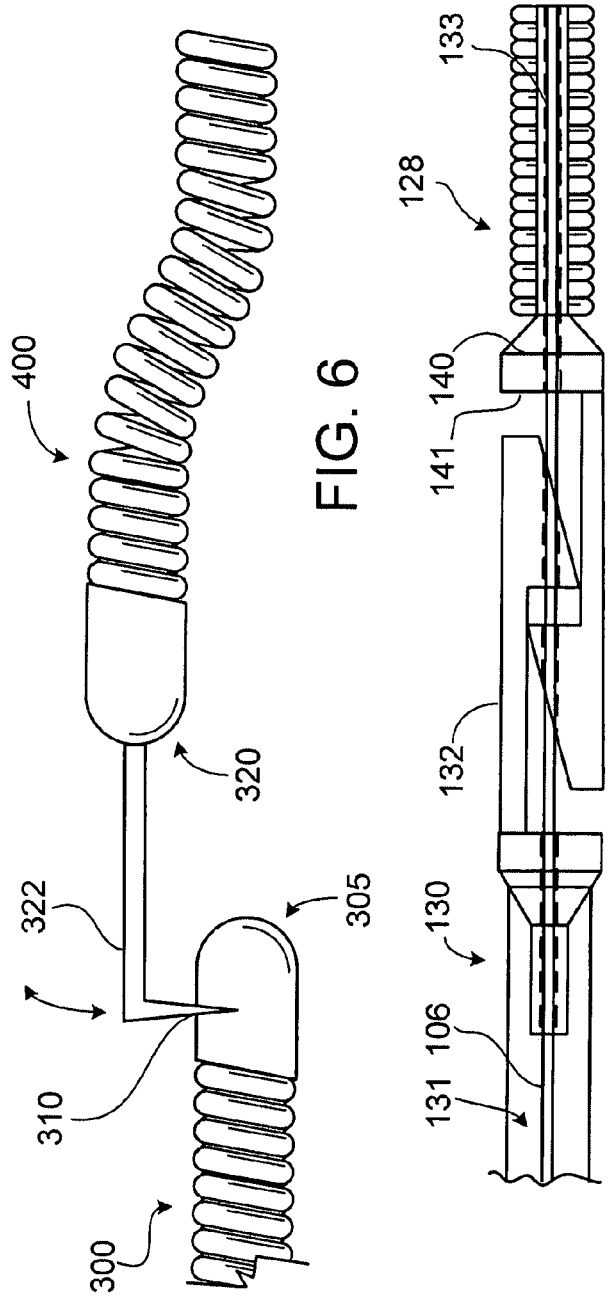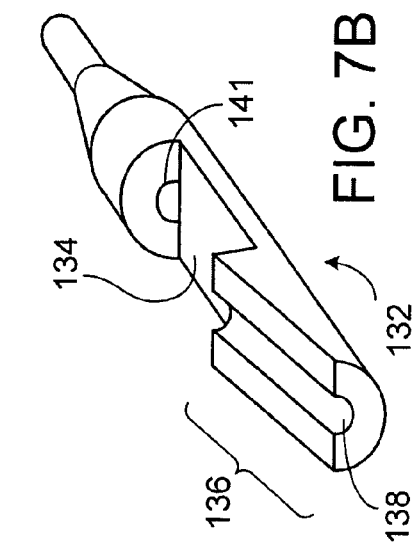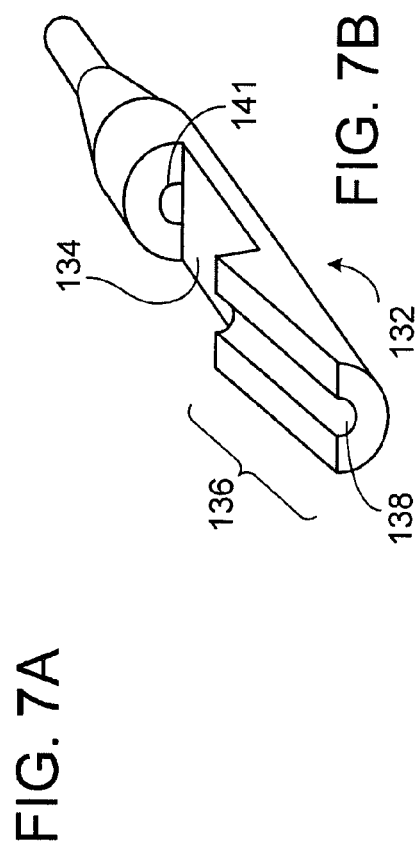

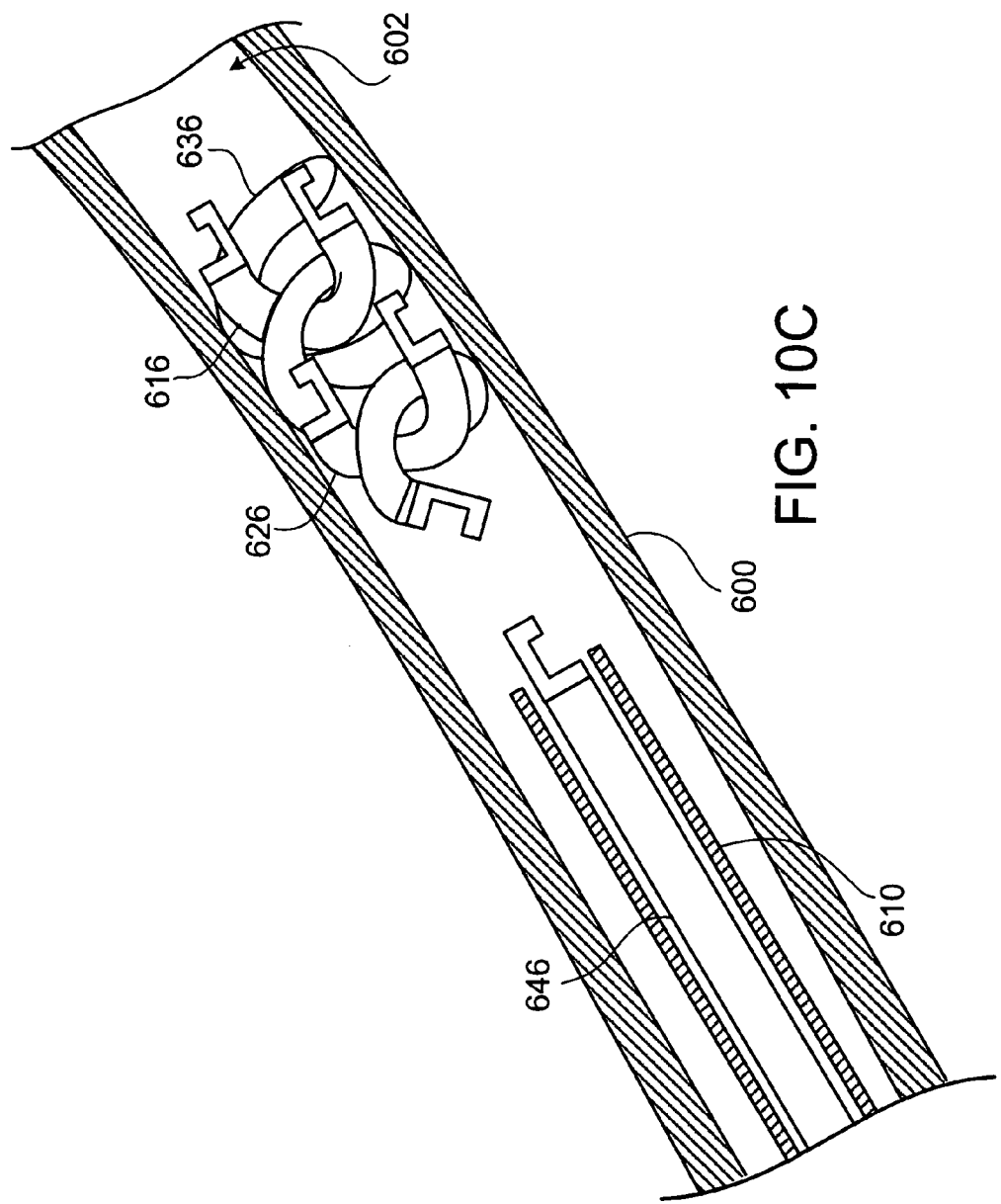

COIL ASSEMBLIES, COMPONENTS AND METHODS

TECHNICAL FIELD

The invention relates to embolic coil assemblies, as well as related components and methods.

BACKGROUND

Embolic coils can be used to occlude vessels in a variety of medical applications.

SUMMARY

The invention relates to embolic coil assemblies, as well as related components and methods.

In one aspect, the invention features a coil assembly that includes at least first and second embolic coils. The first embolic coil has an engaging member, and the second embolic coil has an engaging member that is engaged with the engaging member of the first embolic coil. The first embolic coil differs from the second embolic coil in at least one coil parameter.

In another aspect, the invention features coil assemblies that include three or more embolic coils. Each of the three embolic coils has an engaging member at each end that is adjacent to another embolic coil. The engaging members of each of the three embolic coils are engaged with an engaging member of an adjacent embolic coil. At least one embolic coil differs from at least one other embolic coil in at least one coil parameter.

In a further aspect, the invention features a method that includes inserting a coil assembly into a body lumen of a subject. The coil assembly includes at least first and second embolic coils. The first embolic coil has an engaging member, and the second embolic coil has an engaging member that is engaged with the engaging member of the first embolic coil. The first embolic coil differs from the second embolic coil in at least one coil parameter.

In an additional aspect, the invention features a method that includes inserting a coil assembly into a body lumen of a subject. The coil assembly includes three or more embolic coils. Each of the three embolic coils has an engaging member at each end that is adjacent to another embolic coil. The engaging members of each of the three embolic coils are engaged with an engaging member of an adjacent embolic coil. At least one embolic coil differs from at least one other embolic coil in at least one coil parameter.

In another aspect, the invention features a method of deploying embolic coils to a site. The methods include placing a distal end of a catheter at the site; pushing a coil assembly including at least two (e.g., at least three) embolic coils to the distal end of the catheter; and deploying at least two embolic coils in the coil assembly out of the catheter to the site. At least one embolic coil differs from at least another embolic coil in at least one coil parameter.

Embodiments can include one or more of the following.

The coil parameter can be selected from length, inner diameter, outer diameter, stiffness, secondary shape, and degree of fiber coverage.

The coil assembly can include additional embolic coils (e.g., a third, a fourth, a fifth, or more embolic coils), one or more of which may include engaging members for engaging with engaging members of adjacent embolic coils.

The coil assembly can include a sleeve at least partially surrounding the first and second embolic coils, and optionally any additional embolic coils. The engaging member of an embolic coil (e.g., the first embolic coil) can remain engaged with the engaging member of an adjacent embolic coil (e.g., the second embolic coil) when constrained by the sleeve, and can be capable of disengaging from the engaging member of the adjacent embolic coil when unconstrained by the sleeve.

The assembly can be configured such that movement of the second embolic coil in a proximal or distal direction results in movement of the first coil in the same direction.

The assembly can include a pusher wire. The pusher wire can include an engaging member (e.g., at the distal end of the pusher wire) that is capable of engaging with an engaging member of an adjacent embolic coil.

The embolic coils can be deployed by pushing the coil assembly distally until the distal-most embolic coil (e.g., the first embolic coil) is pushed fully out of the catheter or sleeve, where it disengages from the adjacent embolic coil (e.g., the second embolic coil), optionally repositioning the catheter or sleeve, and then pushing the coil assembly distally until the adjacent embolic coil is pushed fully out of the catheter, where it disengages and is deployed. Where there are additional embolic coils, the method can include pushing each of the embolic coils distally out of the catheter or sleeve such that they disengage and deploy, optionally with repositioning of the catheter occurring between coil deployments. One or more of the embolic coils can be pushed partially out of the catheter and then at least partially retracted back into the catheter, e.g., for repositioning. The method can include determining appropriate coil parameters for treatment of the particular defect (e.g., a vascular defect) and selecting at least first and second embolic coils that have the appropriate coil parameters.

Embodiments can include one or more of the following advantages.

In some embodiments, multiple embolic coils can be disposed within a subject without removing the pusher wire from the subject. This can reduce the complexity, e.g., by reducing the number of steps, and/or enhance the precision of disposing one or more embolic coils within a subject.

In certain embodiments, multiple embolic coils can be disposed within a subject using a continuous process. This can reduce the complexity, e.g., by reducing the number of steps, and/or enhance the precision of disposing one or more embolic coils within a subject.

In some embodiments, multiple embolic coils can be disposed within a subject with a single push of the pusher wire. This can reduce the complexity, e.g., by reducing the number of steps, and/or enhance the precision of disposing one or more embolic coils within a subject.

In certain embodiments, at least one of the multiple embolic coils can differ from at least one other multiple embolic in a coil parameter, such as, for example, length, outer diameter, stiffness, secondary shape, and degree of fiber coverage. One or more of the embolic coils can be selected based on the desired use of the embolic coil(s). Optionally, the order of the embolic coils can also be selected based on the desired use of the embolic coils. For example, each embolic coil can be selected and/or ordered so that the multiple embolic coils as a collection form a particular configuration when disposed within the subject.

Other features and advantages are apparent from the description, drawings and claims.

DESCRIPTION OF DRAWINGS

FIG. 6 is a partial cross-sectional view of an embodiment of a coil assembly.

FIG. 7A is a partial cross-sectional view of an embodiment of a coil assembly.

FIG. 7B is a side view of an embodiment of engaging member.

Like reference symbols in the various drawings indicate like elements.

DETAILED DESCRIPTION

Figure 1:
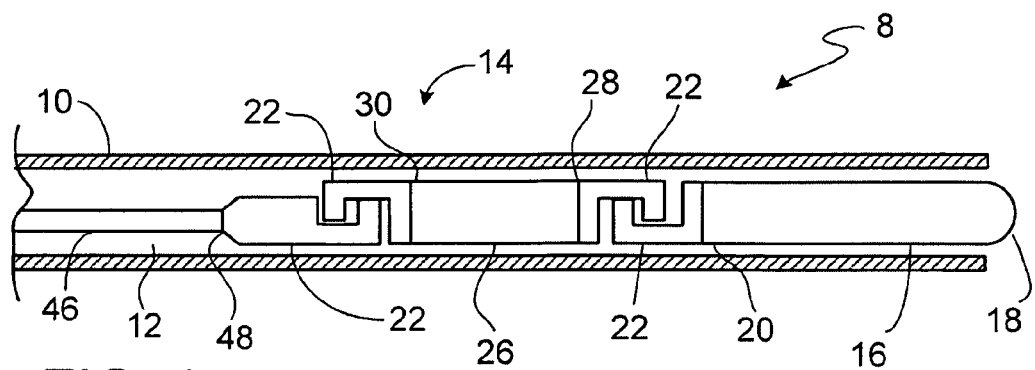
FIG. 1 is a cross-sectional view of an embodiment of a coil assembly.

FIG. 1 shows an embolic coil delivery system 8, which includes a sleeve 10, in this case a catheter. An embolic coil assembly 14 is disposed within a lumen 12 in catheter 10. Embolic coil assembly 14 includes a first embolic coil 16 having a distal end 18, a proximal end 20, and an engaging member 22 at the proximal end 20. Embolic coil assembly 14 further includes a second embolic coil 26 having a distal end 28, a proximal end 30, and engaging members 22 at each end. A pusher wire 46 includes an engaging member 22 at distal end 48.

Figure 2A:
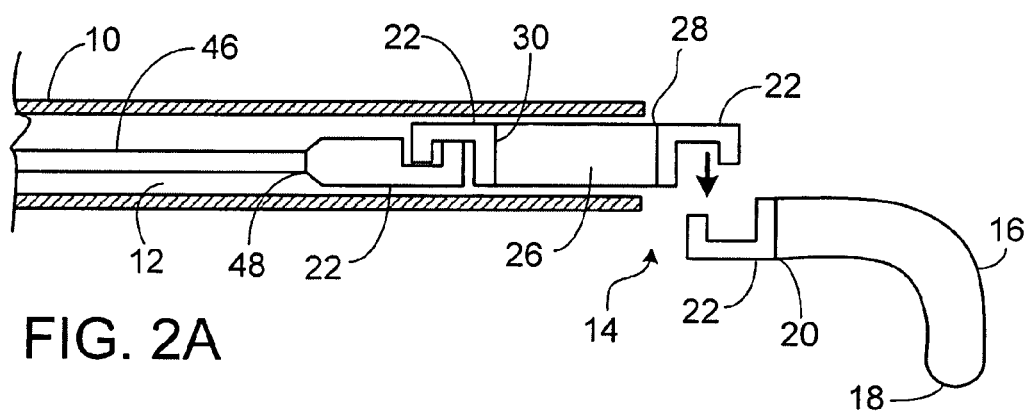
FIG. 2A is a cross-sectional view of an embodiment of a coil assembly illustrating disengagement of the most distal embolic coil.

The engaging member 22 of the first embolic coil 16 is engaged with the adjacent engaging member 22 of the second embolic coil 26. Further, the engaging member 22 at the proximal end 30 of the second embolic coil 26 is engaged with the engaging member 22 of the pusher wire 46. In such an arrangement, the pusher wire 46 can be used to move the embolic coil assembly 14 either proximally or distally within the catheter 10. The catheter 10 prohibits disengagement of the engaged embolic coils 16 and 26 while they are constrained by the catheter 10. As illustrated in FIG. 2A, when embolic coil assembly 14 is moved distally such that the engaging member 22 at the proximal end 20 of the first embolic coil 16 is no longer constrained by the catheter 10, the first embolic coil 16 disengages from the second embolic coil 26 and is deployed. Similarly, the second embolic coil 26 can be so deployed.

Figure 2B:
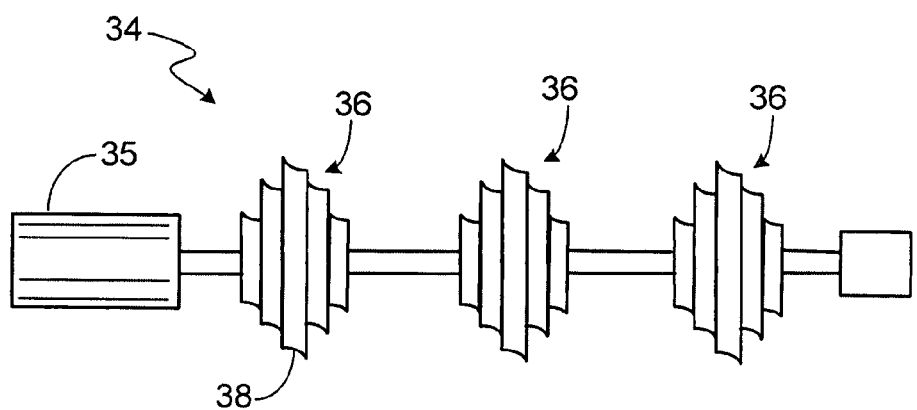
FIG. 2B is a perspective view of an embodiment of a secondary shape mandrel

The embolic coils 16 and 26 differ from each other in at least one coil parameter. For example, the embolic coils may differ from each other in secondary shape. In general, embolic coils have a primary shape and a secondary shape. The primary shape refers generally to the shape of the coil when constrained within the sleeve. The primary shape of an embolic coil generally depends on a number of coil parameters, including, for example, the composition, shape, size, and stiffness of the wire which forms the coil (or braid, where the embolic coil is a braided coil), the outer diameter of the coil, the inner diameter of the coil, and the length of the coil. The secondary shape of an embolic coil refers to the shape of the coil when it is not constrained by the sleeve. As an embolic coil exits the sleeve it can assume its secondary shape. In general, the secondary shape of an embolic coil depends on the process by which the coil was formed, particularly the shape of the mandrel on which the coil was formed and the heat treatment cycle used to shape the coil. For example, a secondary shape mandrel 34, shown in FIG. 2B, can be used to form a primary coil into a secondary shape. The secondary shape mandrel 34 includes a chuck 35 for connecting the mandrel to a device holds the mandrel steady and optionally rotates the mandrel (e.g., a drill). The mandrel 34 includes three shaping locations 36 that have a substantially diamond-shaped cross section. A groove 38 is disposed about the shaping locations 36 to form a continuous, diamond-shaped helix. A primary coil can be positioned in the groove 38 and wound around the shaping locations 36, and subject to a heat cycle to impart the helical diamond shape into the coil. The heat cycle can include, for example, elevating the coil to a temperature of from about 1025° F. to about 1300° F. (e.g., 1100° F.) for a period of time from about 20 minutes to about 40 minutes (e.g., about 30 minutes) to impart the secondary shape into the coil. An embolic coil shaped by one of the shaping locations 36 would represent the diamond-shaped helical coil 54 illustrated in FIG. 3C, described below. The secondary shape mandrel is typically formed of a material capable of withstanding the heat cycle to which the coil will be subjected without significantly softening or changing shape, e.g., stainless steel. The mandrel 34 can include any number of shaping locations and can simultaneously accommodate multiple embolic coils (e.g., at least 4 coils, at least 8 coils, at least 12 coils, or at least 16 coils). The secondary shape imparted by each of the shaping locations can be the same, or can vary.

Other coil parameters play a role in the secondary shape of an embolic coil. Examples of such parameters include the composition, shape, size and stiffness of the wire which forms the coil, the inner and/or outer diameter and the length of the coil, the uniformity of the windings of the coil, the pitch of the primary coil windings, and/or the spacing of the primary coil windings. Typically, the primary shape is selected for deliverability and the secondary shape is selected for the application, e.g., the embolization of an aneurysm.

Figure 3A:
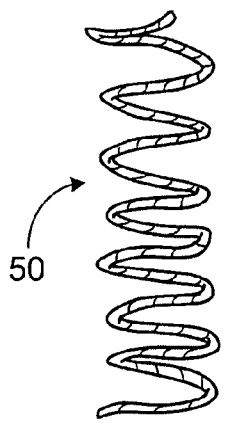
FIG. 3A is a perspective view of an embodiment of an embolic coil.
Figure 3F:
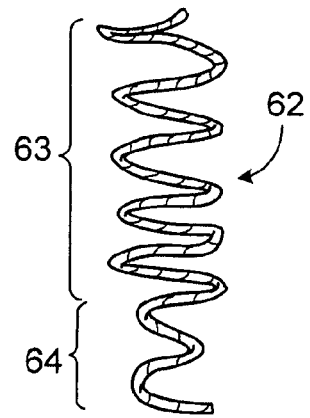
FIG. 3F is a perspective view of an embodiment of an embolic coil.
Figure 3B:
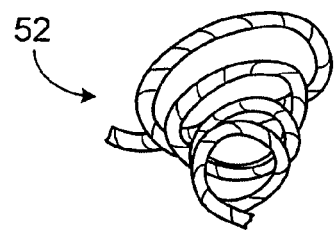
FIG. 3B is a perspective view of an embodiment of an embolic coil.
Figure 3C:
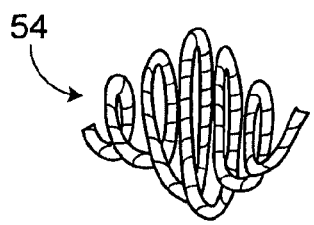
FIG. 3C is a perspective view of an embodiment of an embolic coil.
Figure 3D:
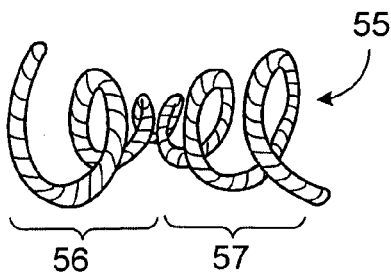
FIG. 3D is a perspective view of an embodiment of an embolic coil.
Figure 3G:
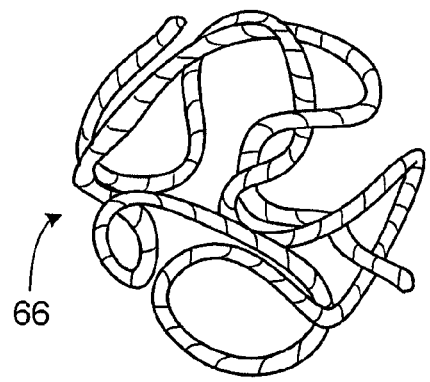
FIG. 3G is a perspective view of an embodiment of an embolic coil.
Figure 3E:
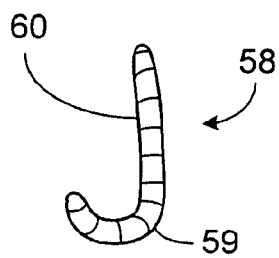
FIG. 3E is a perspective view of an embodiment of an embolic coil.
Figure 3H:
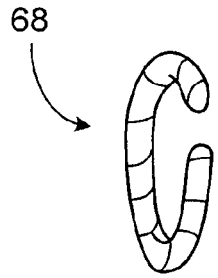
FIG. 3H is a perspective view of an embodiment of an embolic coil.

The embolic coils can have any number of secondary shapes, the choice of which can depend on the particular application in which the embolic coil is to be used. For example, the secondary shape of a first embolic coil and of a second embolic coil can each be independently selected from the group consisting of helical or spiral dual-spiral, dual-diameter spiral, diamond, cone-shaped, random, basket-shaped, straight, C-shaped and J-shaped. As an example, in some of the embodiments, one coil can be have a secondary shape in the form of a basket, while a different coil has a secondary shape in the form of a J. As another example, in certain embodiments one coil can have a helical secondary shape, while a different coil has a diamond or a conical secondary shape. Exemplary secondary shapes are illustrated in FIGS. 3A-3H. For example, FIG. 3A shows an embolic coil 50 with a spiral secondary shape, which can be used, e.g., to provide a supportive framework along a vessel wall and/or to hold other embolic coils that are subsequently delivered to the target site. FIG. 3B shows an embolic coil 52 with a vortex or conical secondary shape, which can be used, e.g., to close the center of a target site such as a vessel or an aneurysm that is to be occluded, optionally in conjunction with an embolic coil or coils, for example, a coil of a different secondary shape. As shown in FIG. 3C, embolic coil 54 can have a diamond secondary shape which can be utilized in a fashion similar to coil 52. FIG. 3D shows a dual-spiral secondary shape 55 in which two conical shapes 56 and 57 meet at their smaller ends. FIG. 3E shows an embolic coil 58 with secondary shape in the form of a J, which can be used, for example, to fill remaining space in an aneurysm not filled by other coils. Optionally, a curved portion 59 of embolic coil 58 can be hooked by the operator (e.g., a physician) into a coil or coil mass that has already been deployed at the target site, with a straight part 60 of embolic coil 58 optionally extending into open space to fill the target site. FIG. 3F shows an embolic coil 62 with a secondary shape in the form of a spiral having a first section 63 with a first helical diameter and a second section 64 with a second helical diameter. Such a coil can be used, for example, to provide a supportive framework along a vessel wall and simultaneously occlude or partially occlude the vessel and/or hold other embolic coils that are subsequently delivered to the target site. FIG. 3G shows an embolic coil 66 having a basket-shaped secondary shape, which can be used, for example, to frame an aneurysm and/or hold or provide a support for other embolic coils that are subsequently delivered to the target site. Any of the shapes just described can be achieved using a braided embolic coil; for example, FIG. 3H shows a braided embolic coil 68 having a secondary shape in the form of a C, which may be used, e.g., in filling an aneurysm. It should be noted that these secondary shapes are approximations, and that the coils may be, for example, a diamond-shape or substantially a diamond shape. Other secondary shapes include random or tangled, generally spherical or spheroid, generally elliptical, clover-shaped, box-shaped. Also included are three-dimensional shapes such as these in which a single coil frames the shape and fills or partially fills the shape. For example, a spherical-shaped coil could have a generally spherical coil frame and be partially filled by the same coil that forms the frame.

In certain embodiments, the embolic coils may differ in length. Suitable coil lengths generally include lengths of, e.g., at least about 2 cm long (e.g., at least about 8 cm long, at least about 15 cm long, or at least about 20 cm long) and/or at most about 30 cm long (e.g., at most about 20 cm long, at most about 15 cm long, or at most about 8 cm long). A coil can, for example, be from about 2 cm to about 30 cm long (e.g., from about 2 cm to about 8 cm long, from about 8 cm to about 15 cm long, from about 15 cm to about 20 cm long, or from about 20 cm to about 30 cm long). As used here, the length of an embolic coil refers to the length of the embolic coil while restrained in a sleeve (i.e. the length of the coil in its primary configuration or shape).

Thus possible coil configurations include, for example, a total coil length (the combined length of all of the embolic coils) of about 30 cm split into one 10 cm coil and ten 2 cm coils; two 5 cm coils and ten 2 cm coils; two 10 cm coils and two 5 cm coils; two 10 cm coils and five 2 cm coils; and three 5 cm coils and five 3 cm coils. The restrained (primary) coil length of an embolic coil may be related to the secondary shape of the coil. For example, a diamond-shaped coil can have a length of no more than about 80 mm (e.g., no more than about 60 mm or no more than about 40 mm) and/or can have a length of no less than about 20 mm (e.g., no less than about 40 mm or no less than about 60 mm). A diamond shaped coil can in some embodiments have a length of from about 20 mm to about 80 mm (e.g., from about 40 mm to about 60 mm). As another example, a spiral-shaped coil can have a length of no more than about 70 mm (e.g., no more than about 60 mm, no more than about 50 mm, no more than about 40 mm, no more than about 30 mm, or no more than about 20 mm) and/or can have a length of no less than about 10 mm (e.g., no less than about 20 mm, no less than about 30 mm, no less than about 40 mm, no less than about 50 mm, or no less than about 60 mm). A spiral-shaped coil can in some embodiments have a length from about 10 to about 70 mm (e.g., from about 20 mm to about 60 mm or from about 30 mm to about 50 mm). As another example, a straight coil can have a length of no more than about 10 mm (e.g., no more than about 7 mm, no more than about 5 mm, or no more than about 3 mm) and/or can have a length of no less than about 2 mm (e.g., no less than about 3 mm, no less than about 5 mm, or no less than about 7 mm). A straight coil can in some embodiments have a length of from about 2 mm to about 10 mm (e.g., from about 3 mm to about 7 mm). As another example, a C-shaped coil can have a length of no more than about 10 mm (e.g., no more than about 7 mm, no more than about 5 mm, or no more than about 3 mm) and/or can have a length of no less than about 2 mm (e.g., no less than about 3 mm, no less than about 5 mm, or no less than about 7 mm). A C-shaped coil can in some embodiments have a length of from about 2 mm to about 10 mm (e.g., from about 3 mm to about 7 mm). As another example, a J-shaped coil can have a length of no more than about 30 mm (e.g., no more than about 25 mm, no more than about 20 mm, or no more than about 15 mm) and/or can have a length of no less than about 10 mm (e.g., no less than about 15 mm, no less than about 20 mm, or no less than about 25 mm). A J-shaped coil can in some embodiments have a length of from about 10 mm to about 30 mm (e.g., from about 15 mm to about 25 mm). As another example, a vortex-shaped or conical-shaped coil can have a length of no more than about 70 mm (e.g., no more than about 67 mm, no more than about 53 mm, or no more than about 35 mm) and/or can have a length of no less than about 30 mm (e.g., no less than about 35 mm, no less than about 53 mm, or no less than about 67 mm). A vortex-shaped or conical-shaped coil can in some embodiments have a length of from about 30 mm to about 70 mm (e.g., from about 35 mm to about 67 mm or from about 35 mm to about 53 mm).

In general, the length of any one coil can be no more than about 80 mm (e.g., no more than about 70 mm, no more than about 60 mm, no more than about 50 mm, no more than about 40 mm, no more than about 30 mm, no more than about 20 mm, no more than about 10 mm, or no more than about 5 mm) and/or can be no less than about 0.5 mm (e.g., no less than about 5 mm, no less than about 10 mm, no less than about 20 mm, no less than about 30 mm, no less than about 40 mm, no less than about 50 mm, no less than about 60 mm, or no less than about 70 mm). In some embodiments, the length of any one coil can be from about 0.5 mm to about 80 mm (e.g., from about 5 mm to about 70 mm, from about 10 mm to about 60 mm, from about 20 mm to about 50 mm, or from about 30 mm to about 40 mm). In some embodiments, the length of all the coils, in total, can be no more than about 60 cm (e.g., no more than about 50 cm, no more than about 40 cm, no more than about 30 cm, no more than about 20 cm, no more than about 10 cm, or no more than about 8 cm). Generally, the length of the coils, in total, is selected in part to prevent the amount of force used to push the coil assembly from becoming too large.

The coils may differ in the diameter of the wire from which they are formed. For example, the coils may be formed of wire, e.g., platinum, platinum/tungsten alloy or stainless steel wire, having a diameter of between about 0.001 inch to about 0.005 inch in diameter. One coil may be formed of wire having a diameter of between about 0.001 inch to about 0.0025 inch in diameter, while another coil may be between about 0.003 inch to about 0.005 inch in diameter. The difference in wire diameter can result in a difference in the outer diameter of the first coil and second coil (taken in their primary shapes), given a constant inner diameter of the first and second coils. For example, the outer diameter of one of the first coil and second coil may be between about 0.013 inch to about 0.015 inch and the other of the first coil and second coil may be between about 0.010 inch to about 0.012 inch while sharing a constant inner diameter.

The outer diameter of the coils may differ regardless of the inner diameter of the coils. The outer diameter of a coil refers to the outer diameter of the coil when in its secondary configuration. In certain embodiments, the outer diameter of the coils can be no more than about 14 mm (e.g., no more than about 12 mm, no more than about 10 mm, no more than about 8 mm, no more than about 6 mm, no more than about 4 mm, or no more than about 2 mm) and/or can be no less than about 1 mm (e.g., no less than about 2 mm, no less than about 4 mm, no less than about 6 mm, no less than about 8 mm, no less than about 10 mm, or no less than about 12 mm). In some embodiments, the outer diameter of the embolic coils can be from about 1 mm to about 14 mm (e.g., from about 2 mm to about 12 mm, from about 4 mm and to about 10 mm, or from about 6 mm and to about 8 mm). In some embodiments, one embolic coil can have an outer diameter no more than about 6 mm (e.g., no more than about 5 mm, no more than about 4 mm, no more than about 3 mm, or no more than about 2 mm) while another embolic coil can have an outer diameter of not less than about 8 mm (e.g., not less than about 10 mm or not less than about 12 mm).

The stiffness of the coils may be varied. It will be recognized that certain other parameters will affect the stiffness of the coils, for example, the composition and the diameter of the wire from which the coil is formed. The diameter of a mandrel around which the coil is formed (in other words, the inner diameter of the coil) may affect the stiffness. Also, additional treatment of the coil once formed can affect the stiffness. For example, subjecting a coil to heat and then cooling the coil may result in stiffening of the coil. Coil stiffness may vary between about 0.001 lbf and about 0.004 lbf. Coil stiffness can be measured by measuring the force required to compress the outer coil 5% of the main secondary coil diameter. For example, a dynamic testing machine, such as is available from Instron Corp., can be utilized to test coil stiffness. A main outer diameter of a secondary coil is removed from the secondary coil and placed in the gripping mechanism of the testing machine such that only half of the diameter (a semi-circle shape) is exposed. The sample is placed directly below an anvil-like fixture that compresses down on the surface of the outer diameter. The force required to compress the sample by 5% of the overall main outer diameter is measured.

In some embodiments, some or all of the embolic coils may include fibers. Exemplary fiber materials include polyethylene terephthalate (e.g., Dacron®), nylon, collagen and/or cotton fibers, which may promote thrombosis by providing a substrate for clot formation. The degree of fiber coverage may be varied. For example, some of the embolic coils may have fibers while others do not. In some embodiments, the embolic coils may each have fibers but have different amounts of fibers for a given length of coil. The fibers may be, for example, of the same or different length (generally between about 0.5 mm to about 5 mm), stiffness, and/or diameter. The spacing between fiber bundles and the fiber densities (i.e. number of fiber filaments per fiber bundle) are additional factors capable of variation; one coil can have bundles having greater numbers of fibers than a different coil but have the bundles spaced farther apart, resulting in the same number of fibers per length of coil but a different distribution of fiber coverage on each coil.

While embodiments that contain two embolic coils have been described, the embolic coil delivery systems can include more than two embolic coils (e.g., three or more, four or more, five or more, or six or more embolic coils). In such embodiments, at least two of the embolic coils differ from each other in at least one coil parameter. In certain embodiments, three or more, four or more, five or more, or six or more embolic coils can differ from each other in at least one coil parameter; further, the coil parameters that differ may be the same coil parameter or may be two or more different coil parameters (e.g., three or more, four or more, five or more, or six or more different coil parameters).

The embolic coils generally include at least one engaging member for engaging with an adjacent embolic coil, and may optionally include two engaging members for engaging with adjacent embolic coils or pusher wires one either side of the embolic coil. The engaging members generally are configured such that one member reversibly accepts a portion of a corresponding member. Configurations include an engaging member having an open receiving slot generally perpendicular to the longitudinal axis of the coil and corresponding engaging member having a hook adapted to enter and exit an open receiving slot generally perpendicular to the longitudinal axis of the coil, and also include engaging members having an outer portion of a generally cylindrical shape, a middle portion adapted to accept a generally cylindrical outer portion of an adjacent corresponding engaging member, and an inner portion adapted for attaching to the coil (where "outer" refers to the portion of the engaging member distant from the coil to which it is attached and "inner" refers to the portion nearest the coil). The engaging member of one end of a coil may be, but need not be, the same as the engaging member at a different end of the coil, where the coil has two engaging members. Each coil and each engaging member may further include a channel or lumen extending longitudinally, with a control wire extending through the channels to further engage the coils.

Figure 4A:
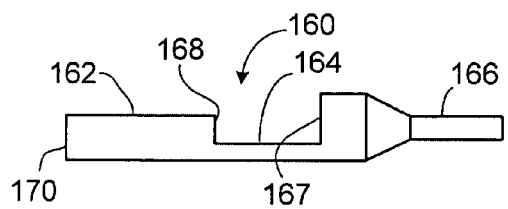
FIG. 4A is a side view of an embodiment of engaging member.
Figure 4B:
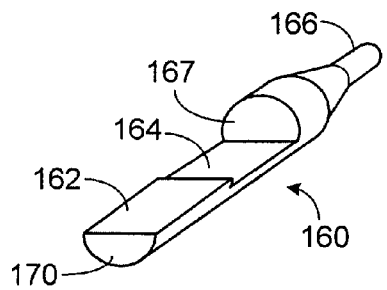
FIG. 4B is a perspective view of the embodiment of FIG. 4A.
Figure 4C:
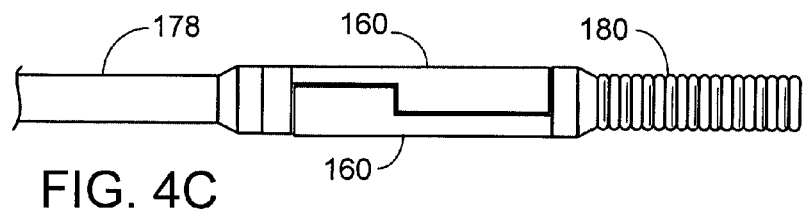
FIG. 4C is a partial cross-sectional view of an embodiment of a coil assembly.
Figure 5A:
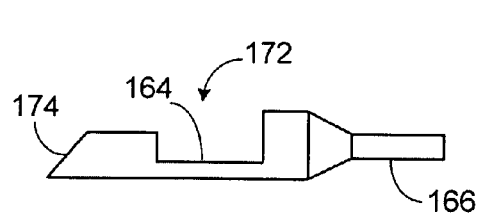
FIG. 5A is a side view of an embodiment of engaging member.
Figure 5B:
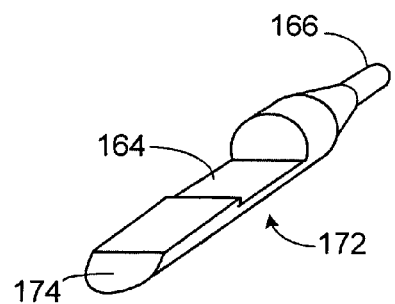
FIG. 5B is a perspective view of the embodiment of FIG. 5A.
Figure 5C:
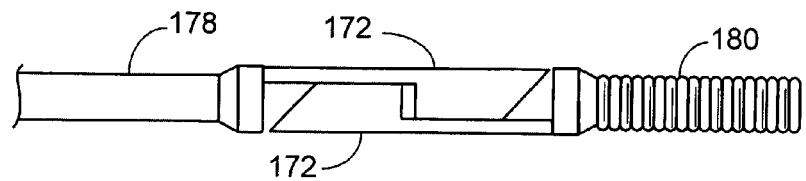
FIG. 5C is a partial cross-sectional view of an embodiment of a coil assembly.

Examples of engaging member embodiments are illustrated in FIGS. 4-6. FIGS. 4A and 4B show side and perspective views, respectively, of an embodiment of an engaging member 160. Engaging member 160 is generally cylindrical in shape with a surface 162 which may be cut or milled away to allow the surface to mesh with receiving area 164 on an adjacent engaging member. Connecting end 166 is adapted to be connected to an embolic coil or pusher wire, and may be any suitable shape, e.g., cylindrical. Vertical mating surface 168 is adapted to meet a similar vertical mating face on an adjacent engaging member to allow one engaging member to pull the other when the first engaging member is pulled, while end surface 170 pushes against mating surface 167 when the first engaging member is pushed. FIG. 4C shows a pair of engaging members as described in FIGS. 4A and 4B when engaged, in this case engaging a pusher wire 178 and an embolic coil 180. FIGS. 5A, 5B and 5C show an interlocking member 172 having an end surface 174 that is ramped. This design can, for example, permit assembly ease in placing the coils into a catheter or introducer sheath.

In certain embodiments, the engaging members of adjacent embolic coils that are engaged with one another have different configurations from each other. For example, as shown in FIG. 6, each of the pair of engaging members has a differing configuration. A coil 300 has an engaging member 305 which has a slot 310 located thereon. Slot 310 is configured to receive a hook 322 of an engaging member 320, located at an end of coil 400.

In some embodiments, an embolic coil assembly may also include a control wire. The control wire can permit the coils to remain engaged until the control wire is removed and the coil is not constrained by a catheter or introducer sleeve. For example, FIGS. 7A and 7B show an embolic coil assembly 130 in which a coil 128 is engaged with a pusher wire 130 by engaging members 132 in combination with a control wire 106. Each engaging member 132 includes a ramped face 136 with a slot 138 and a longitudinally-extending passageway 140 for receiving control wire 106. Control wire 106 extends through lumens 131 and 133 in the pusher wire 130 and in coil 128, respectively. Engaging members 132 cannot disengage, even when unconstrained by a sleeve, until control wire 106 is pulled out of opening 141 of channel 140. When engaging members 132 are not constrained by a sleeve and control wire 106 has been pulled out of opening 141 of channel 140, the coil 120 will disengage from the pusher wire 130. Such a control wire may be incorporated into any of the other engaging member embodiments.

Figure 8:
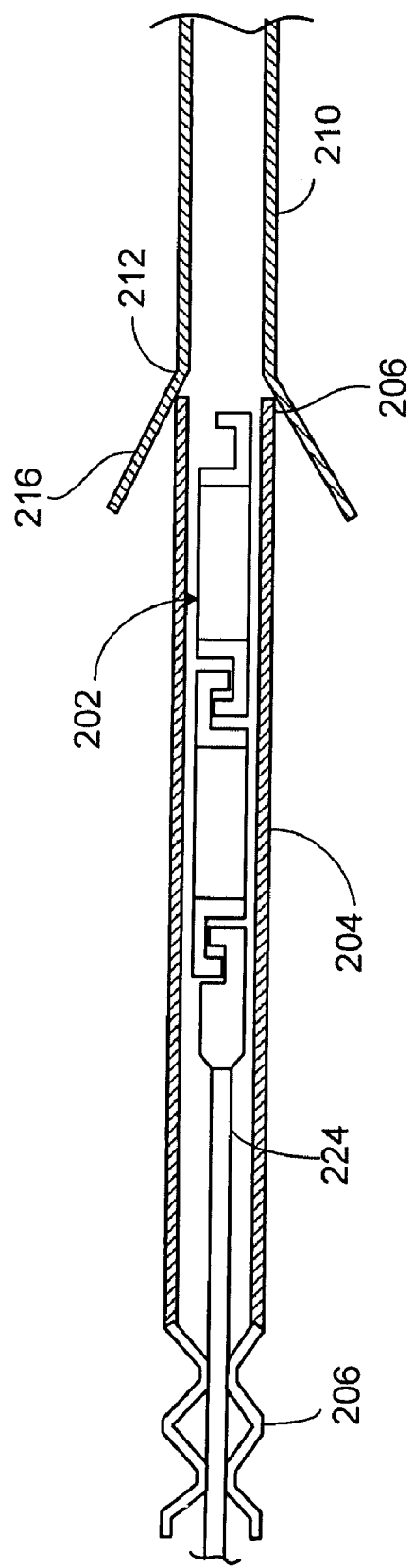
FIG. 8 is a cross-sectional side view of an embodiment of a coil assembly, introducer sheath and catheter.

FIG. 8 illustrates an embolic coil assembly delivery system in which an embolic coil assembly 202 is contained in an introducer sleeve 204 which is separate from catheter 210. Optionally, the introducer sleeve 204 includes a locking portion 206, e.g., a portion of the introducer sleeve that has been twisted under heat to deform and grip the pusher wire and/or coil assembly, to lock a pusher wire 224 and/or coil assembly 202 in sleeve 204. This may prevent the coil assembly from moving longitudinally in the sleeve and possibly out of the sleeve before such is desired. Such a locking portion can be unlocked, e.g., by untwisting the sheath, to allow the pusher wire/coil assembly to move freely.

Generally, the catheter 210 is first inserted into a body lumen of a subject, for example, through an incision into the femoral artery, and moved through the body until its distal end is at a target location, for example, the opening of an aneurysm. Once in place, a distal tip 206 of sleeve 204 is placed into a hub 216 attached to a proximal end 212 of the catheter and the embolic coil assembly is pushed by means of pusher wire 224 into catheter 210 and to the distal end of the catheter for delivery to the target site. The pusher wire is then used to push the embolic coil assembly out of the distal tip of the catheter such that individual coils disengage from the assembly and deploy into the target area. Alternatively, the pusher wire may be used to hold the coil assembly in place while the catheter is retracted, thus permitting self-disengagement of individual coils. Where a control wire is included, it may be retracted either before or after pushing the coils out of the catheter or retracting the catheter.

Figure 9A:
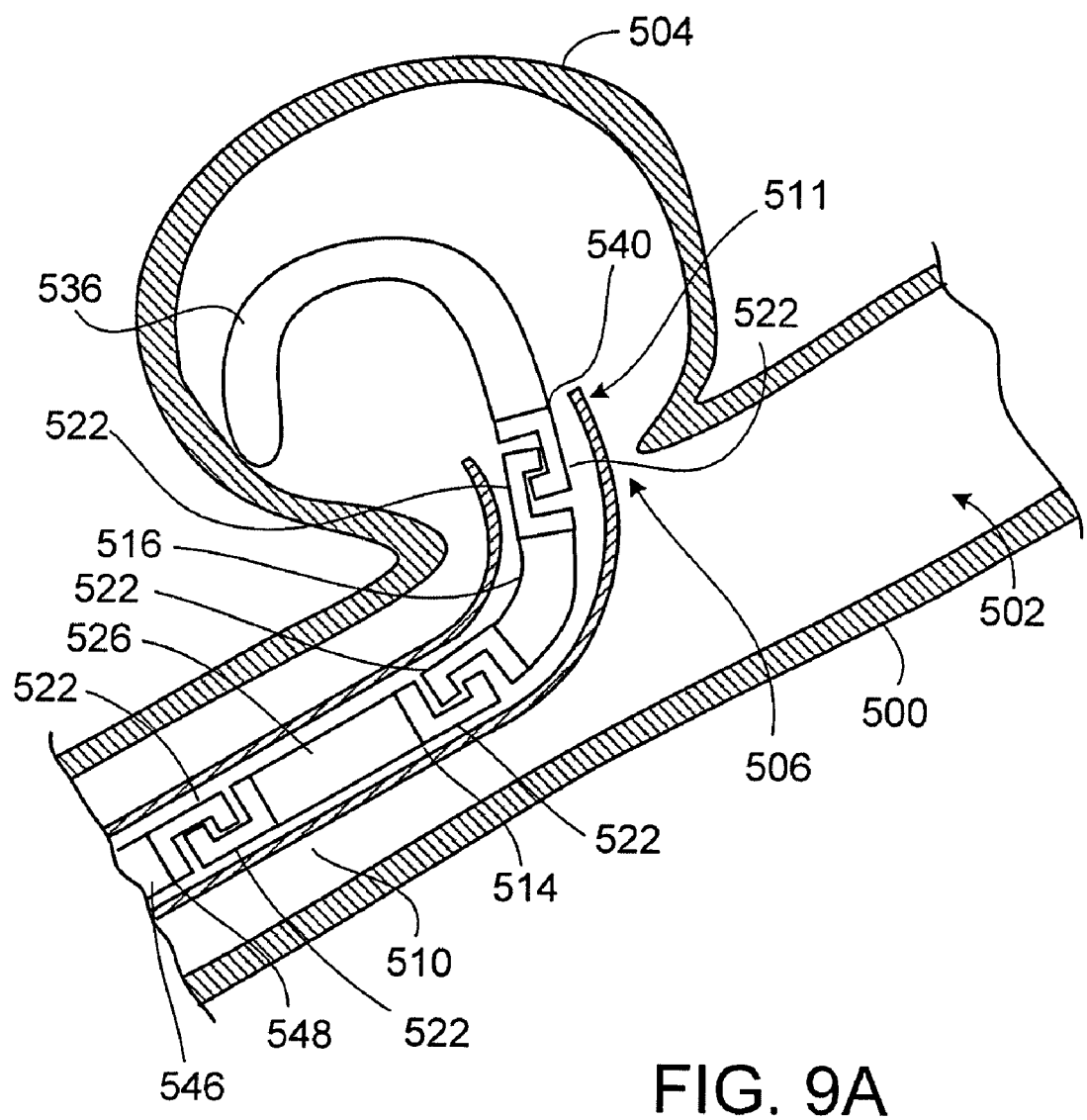
FIG. 9A-C illustrate an embodiment of a method.
Figure 9B:
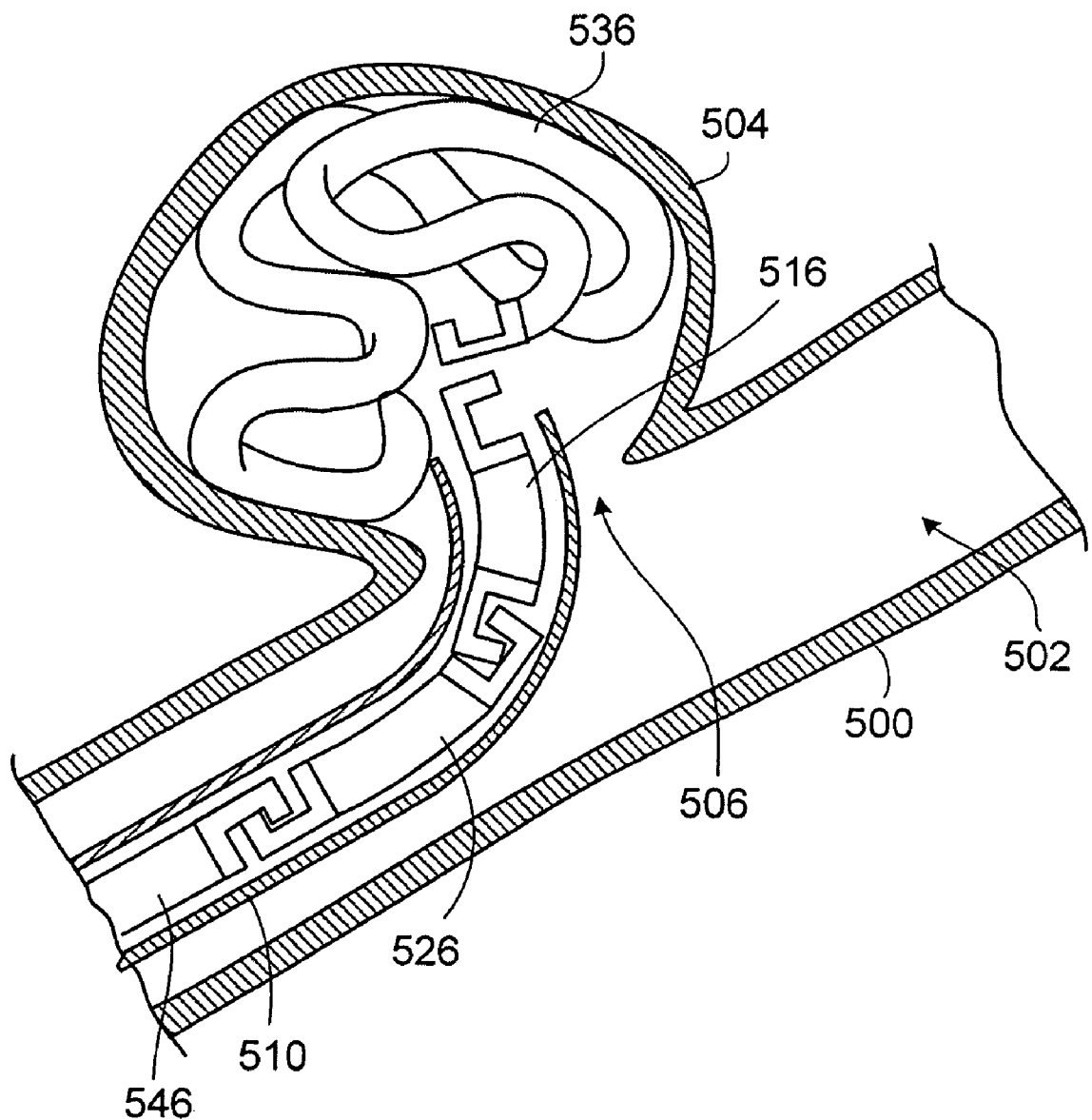
Figure 9C:
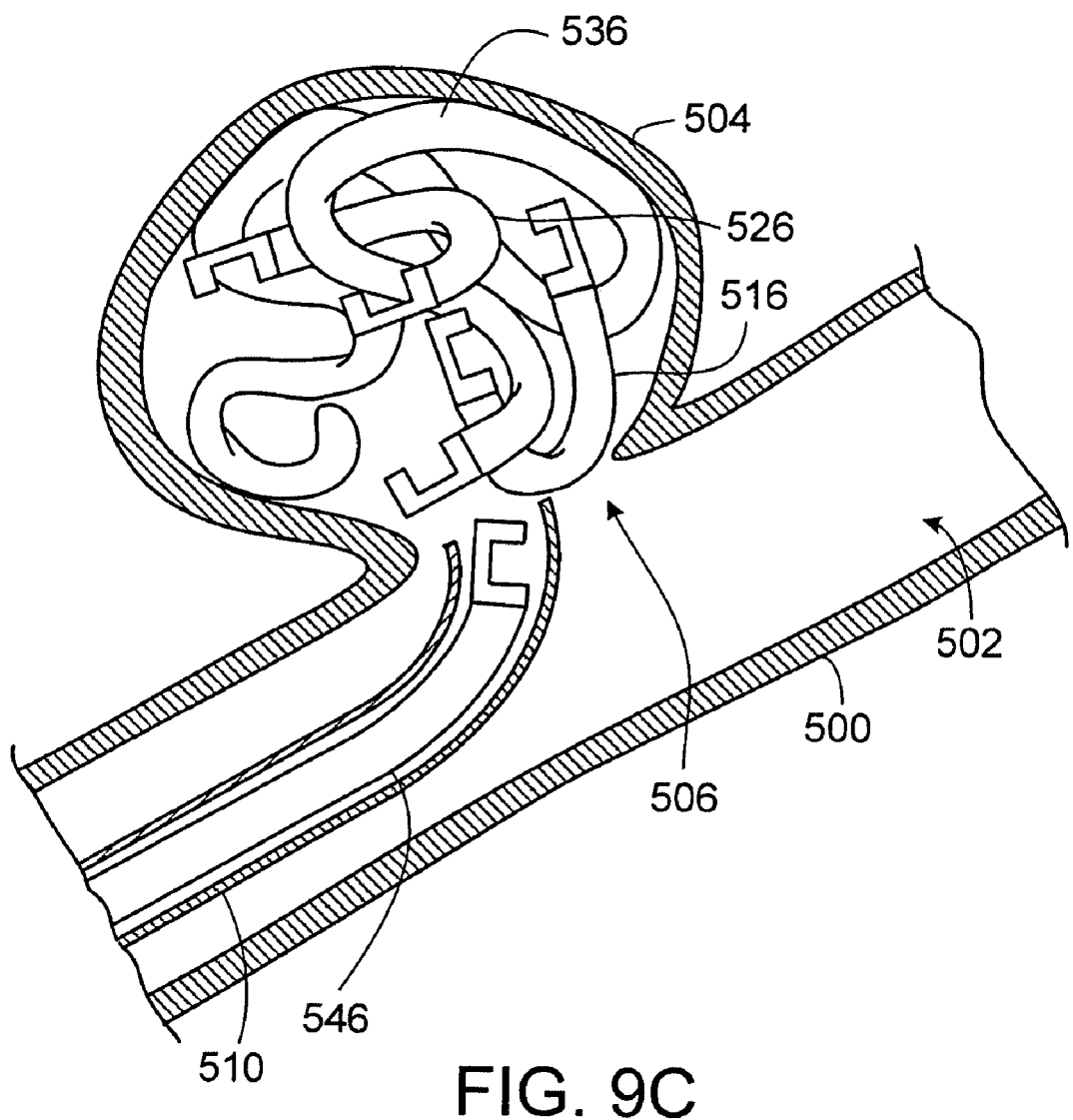

FIGS. 9A-C illustrate an embodiment of a method for treatment of an aneurysm. A catheter 510 is inserted into the body and guided through a lumen 502 in a vessel 500 to an opening 506 in an aneurysm 504. An embolic coil assembly 514 is inserted into the catheter for deployment into the aneurysm. Embolic coil assembly 514 includes a long coil 536 with an engaging member 522 at a proximal end 540 and two shorter coils 516 and 526, each having engaging members 522 at each end. The coils are selected to accomplish particular tasks with respect to treating the aneurysm. For example, long coil 536 is selected of a sufficient length and secondary shape to frame the embolism to add strength and prevent the aneurysm from rupturing, to begin sealing off the opening 506, and to provide a framework to which shorter coils 516, 526 can attach themselves. Shorter coils 516, 526 have a secondary shape in the form of a J to enable each to be hooked onto this framework and are sufficiently flexible to enable them to pack together densely to fill the voids in the aneurysm. In certain embodiments, the J-shaped coils will themselves be long (e.g., from about 15 mm to about 30 mm) as well as soft and flexible. This can enable a physician to custom fill vessels or aneurysms as desired to achieve a desired density of packing.

A pusher wire 546 with an engaging member 522 at its distal end 548 is engaged to coil 526. The pusher wire is used to push embolic coil assembly 514 to the distal end 511 of catheter 510 so that the long coil 536 extends partially out of the catheter. The long coil 536 begins to assume its secondary shape as it exits the catheter. At this point, should repositioning be desired, the embolic coil assembly 514 can be retracted into the catheter by pulling back on the pusher wire 546.

Once in the proper position, as illustrated in FIG. 9B, the embolic coil assembly 514 is pushed sufficiently far distally that the long coil 536 passes entirely out of catheter 510, disengages and assumes its secondary basket shape and frames the aneurysm. At this point, the catheter 510 can be left in position and the remaining coils 516, 526 can be deployed. As seen in FIG. 9C, embolic coils 516 and 526 have a secondary shape in the form of a J to hook onto the long coil 536 and extend into and fill voids in the aneurysm. The pusher wire 546 need not be withdrawn to permit insertion of the additional coils. This may provide for shorter times of treatment and/or less movement of materials through the catheter, given the lack of a requirement for removing the pusher wire, inserting a J-shaped coil, reinserting the pusher wire and pushing the coil to the distal tip of the catheter, and may lead to superior results.

Figure 10A:
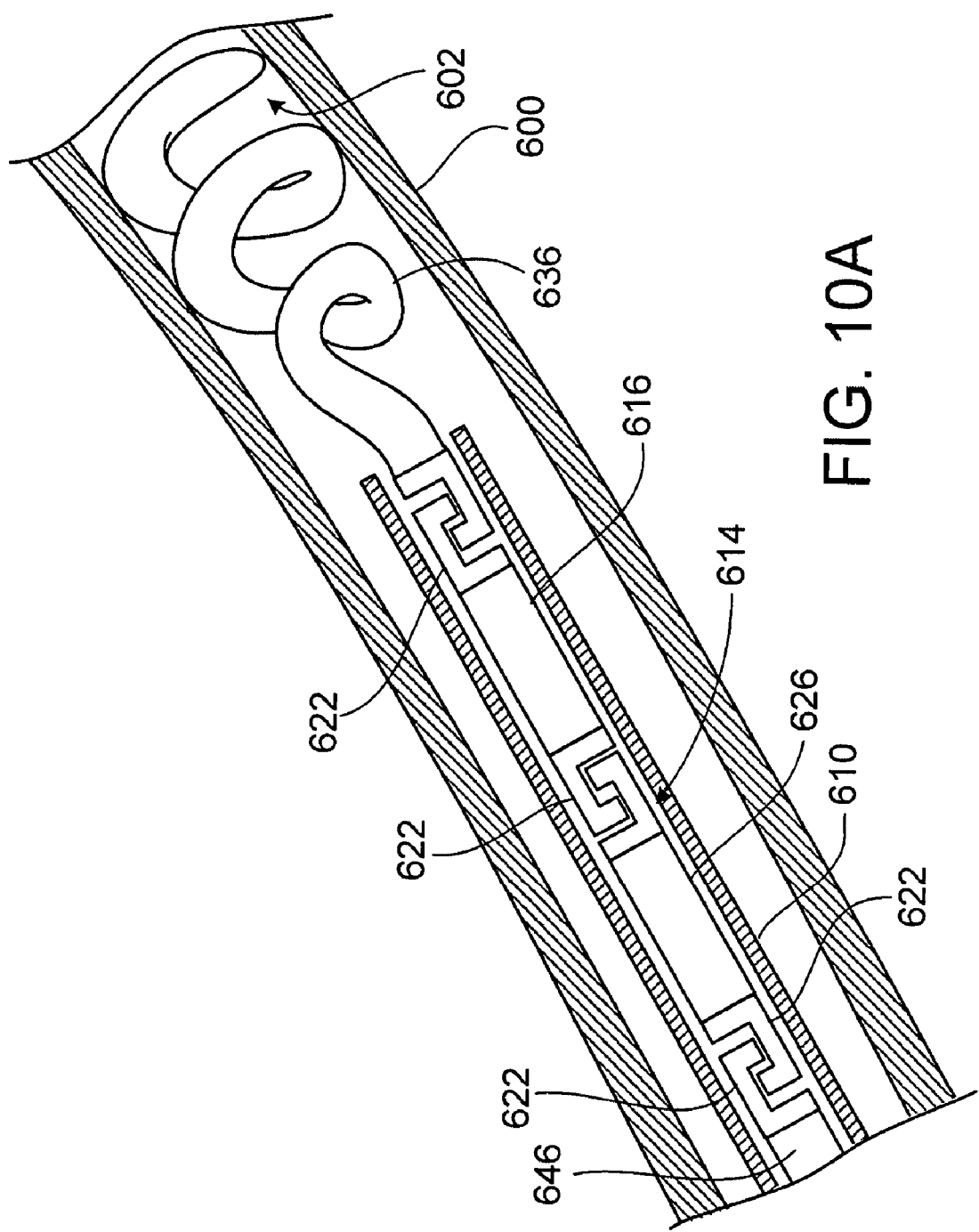
FIG. 10 illustrate an embodiment of a method.
Figure 10B:
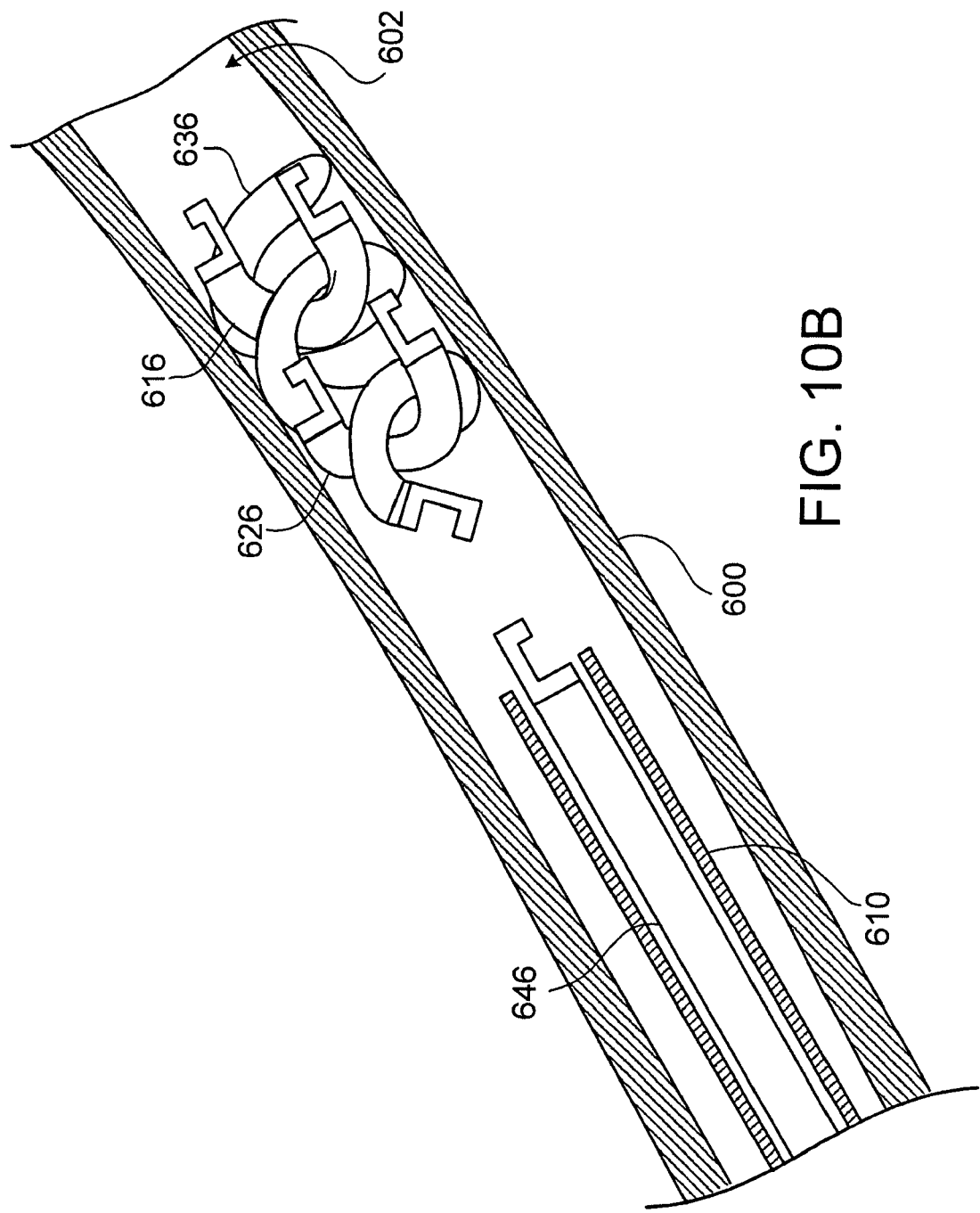
Figure 11:
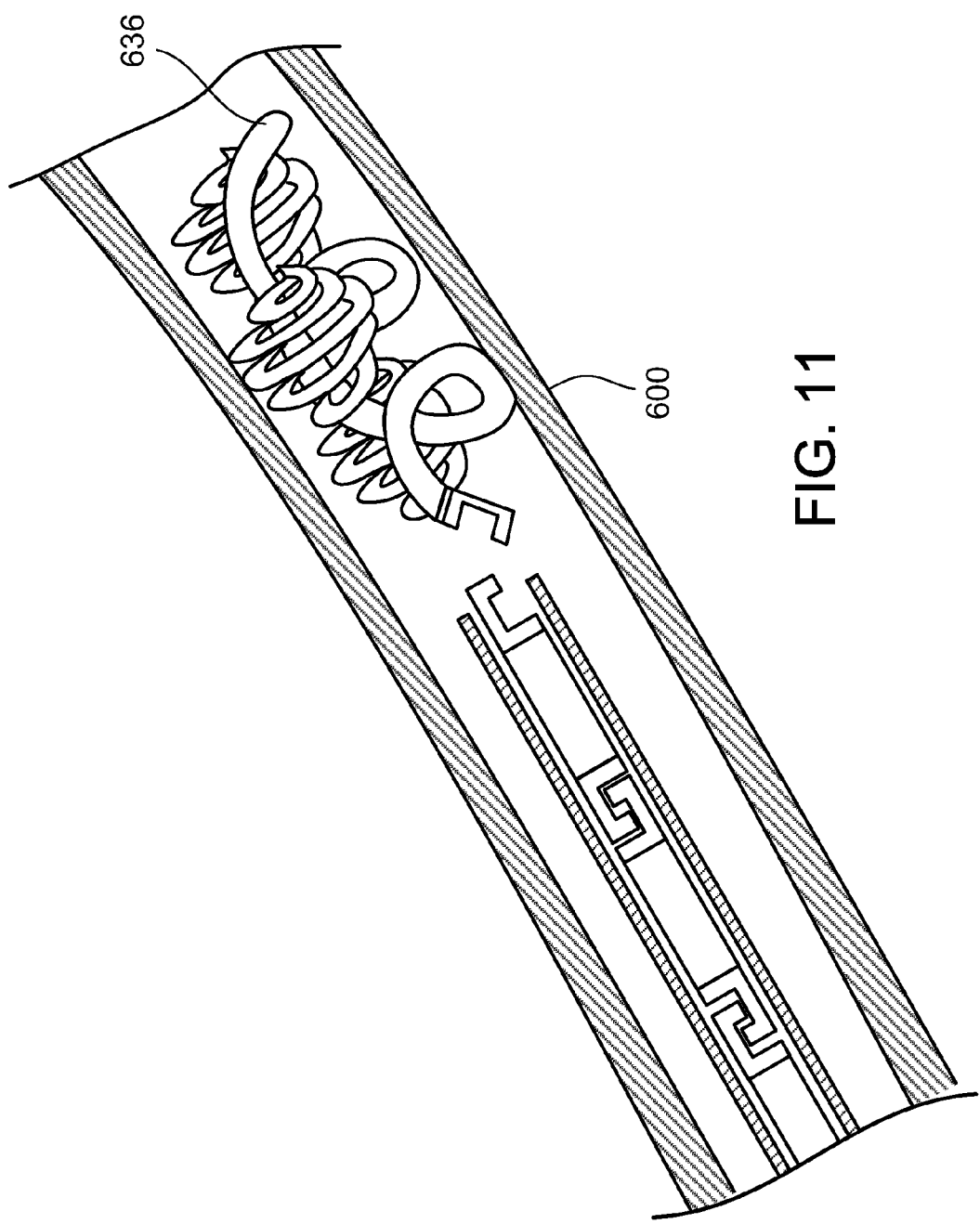
FIG. 11 illustrates an embodiment of a method.

FIGS. 10A-C show the occlusion of a vessel 600, with a long coil 636 having a helical secondary shape being first deployed (FIG. 10A, 10B), followed by a first coil 616 having a secondary shape in the form of a C that can, for example, hook itself into the helical coil 636, and followed by second coil 626 having a secondary shape in the form of a J such that, for example, the hooked portion of the J shape can attach itself to the helical coil and the straight portion can extend into the opening to occlude the vessel 600. Additional coils could be added to the embolic coil assembly, such as coils having as secondary shapes diamonds, vortexes or the like to better occlude the central part of the vessel and interweave themselves with the helical coil (see, e.g., FIG. 11).

While certain embodiments have been described, others are possible.

As an example, some or all of the embolic coils in the embolic coil assembly may have secondary shapes other than those disclosed above. For example, other suitable secondary shapes, and methods for creating embolic coils having such shapes, are discussed in U.S. Pat. Nos. 4,994,069, 6,231,586, 6,322,576 and 6,635,069, each of which is hereby incorporated by reference.

As another example, one or more of the embolic coils may include a coating, e.g., a polymer coating, for example, a lubricous coating, that may reduce friction between the coil and the catheter and allow for easier pushing of the coil.

As an additional example, one or more coils may further include a therapeutic substance, e.g., a drug, for delivery to the target site along with the coil.

As a further example, the embolic coils may differ in more than one coil parameter, for example, two, three, four, five or more coil parameters may be different.

As another example, more than two of the embolic coils may differ in one or more coil parameters, for example, three, four, five, or more coils, even each of the coils, may differ from each other in one or more coil parameters.

At least one of the embolic coils may be made in whole or in part of helical wire.

At least one of the coils may be made in whole or in part of braided wire.

At least one of the coils may include a radiopaque marker, which may consist of or be a part of the engaging member.

At least one of the embolic coils may be formed of a polymer, e.g., a biocompatible polymer. Exemplary polymers include polyethylene, polyurethane, and polypropylene.

Moreover, while embodiments of the engaging members have been described as being generally cylindrical in cross-sectional shape, the engaging members may have other configurations, for example, pentagonal or hexagonal. Also, the engaging members may have different engaging configurations than those disclosed above. Other suitable engaging members are described in U.S. Pat. Nos. 5,250,071, 5,304,195, 5,800,453, 5,800,455, 5,891,130, 5,925,059, 6,099,546, RE37,117 E, and in WO 94/06503, each of which is hereby incorporated by reference.

Further, in some embodiments, a saline flush can be used to deliver an embolic coil from the sleeve rather than, or in addition to, the pusher wire.

Still further, in some embodiments, embolic coils can be used in conjunction with other embolic devices. Other embolic devices include, for example, embolic particles such as those described in U.S. Published Patent Application No. 2003/0185896 A1, published on Oct. 2, 2003, and in U.S. Published Patent Application No. US 2004/0096662 A1, published on May 20, 2004, each of which are hereby incorporated by reference. Other embolic devices also include, for example, embolic gels such as described, for example, in U.S. patent application Ser. No. 10/927,868, filed on Aug. 27, 2004, and entitled "Embolization", which is hereby incorporated by reference.

In general, embolic coils may be used to treat a variety of conditions. For example, embolic coils may be used generally to treat neurological and/or peripheral conditions such as to occlude a vessel or to treat an aneurysm, an arteriovenous malformation (AVM), or a traumatic fistula. Embolic coils can be used to embolize a tumor, for example, a liver tumor. Embolic coils can be used in transarterial chemoembolization (TACE).

Other embodiments are in the claims.

What is claimed is:

1. A coil assembly, comprising:
   a first embolic coil having a proximal end interlocking member;
   a second embolic coil having a distal end interlocking member engaged with the proximal end interlocking member of the first embolic coil, the second embolic coil having a predetermined secondary shape configured to be received at least partially within and engage a predetermined secondary shape of the first embolic coil when the respective first and second embolic coils are released within an aneurysm sac; and
   a delivery catheter containing the first embolic coil and the second embolic coil, the first embolic coil disposed farther from a proximal end of the catheter than the second embolic coil, wherein the proximal end interlocking member of the first embolic coil remains engaged with the distal end interlocking member of the second embolic coil when the respective coils are constrained within the delivery catheter, and the interlocking member of the first embolic coil is configured to disengage from the interlocking member of the second embolic coil when the respective coils are released out of a distal end opening of the delivery catheter;
   wherein the predetermined secondary shape of the first embolic coil is selected from a group consisting of helical, diamond, cone-shaped, basket-shaped, and spiral; and
   wherein the predetermined secondary shape of the second embolic coil is selected from a group consisting of C-shaped, straight, diamond, and J-shaped.

2. The coil assembly of claim 1, wherein the first embolic coil differs from the second embolic coil in at least one coil parameter selected from the group consisting of length, inner diameter, outer diameter, stiffness, and degree of fiber coverage.

3. The coil assembly of claim 1, wherein movement of the second embolic coil in a proximal or distal direction results in movement of the first embolic coil in the same direction.

4. The coil assembly of claim 1, further comprising a pusher wire including a distal end interlocking member, wherein the second embolic coil further comprises a proximal end interlocking member engaged with the distal end interlocking member of the pusher wire.

5. The coil assembly of claim 1, further comprising a third embolic coil having a distal end interlocking member, wherein the second embolic coil further comprises a proximal end interlocking member engaged with the distal end interlocking member of the third embolic coil.

6. The coil assembly of claim 1, wherein the first and second embolic coils differ in length.

7. The coil assembly of claim 6, wherein the first embolic coil is at least 50 cm long and the second embolic coil is no more than 10 cm long.

8. The coil assembly of claim 1, wherein the secondary shape of the first embolic coil is the basket shape and the secondary shape of the second embolic coil is the J-shape.

9. The coil assembly of claim 1, wherein the secondary shape of the first embolic coil is the helical shape and the secondary shape of the second embolic coil is the diamond.

10. The coil assembly of claim 1, wherein the first embolic coil and the second embolic coil differ in stiffness.

11. The coil assembly of claim 1, wherein the first embolic coil and the second embolic coil differ in outer diameter.

12. The coil assembly of claim 11, wherein the outer diameter of one of the first embolic coil and second embolic coil is at least about 0.013 inch and the other of the first embolic coil and second embolic coil is at most about 0.012 inch.

13. The coil assembly of claim 1, further comprising an introducer sheath configured to contain the first and second embolic coils in an engaged state, the introducer sheath adapted to abut the proximal end of the delivery catheter to permit passage of the first and second embolic coils from the introducer sheath to the delivery catheter without the first and second embolic coils disengaging.

* * * * *